US011883604B2

(12) United States Patent
Godara et al.

(10) Patent No.: US 11,883,604 B2
(45) Date of Patent: Jan. 30, 2024

(54) GAS MIXING SYSTEM FOR MEDICAL VENTILATOR

(71) Applicant: Covidien LP, Mansfield, MA (US)

(72) Inventors: Neil Godara, Milton (CA); Matthew J. Phillips, Carlsbad, CA (US); Amand Kasimatis, Carlsbad, CA (US); Donald J. Novkov, Encinitas, CA (US); Patrick S. Ryan, Toronto (CA); Amanda Centazzo-Colella, Montreal (CA); Laurentiu Murtescu, Vaughan (CA); Amanda A. Hartley, Caledon (CA); Michael J. N. Matsumoto, Toronto (CA); Jacques L. Vassal, Montreal (CA); Danian Yang, Vaughan (CA); Randy Yang, Richmond Hill (CA)

(73) Assignee: Covidien LP, Mansfield, MA (US)

(*) Notice: Subject to any disclaimer, the term of this patent is extended or adjusted under 35 U.S.C. 154(b) by 365 days.

(21) Appl. No.: 17/226,752

(22) Filed: Apr. 9, 2021

(65) Prior Publication Data
US 2021/0316105 A1   Oct. 14, 2021

Related U.S. Application Data

(60) Provisional application No. 63/079,518, filed on Sep. 17, 2020, provisional application No. 63/008,508, filed on Apr. 10, 2020.

(51) Int. Cl.
*A61M 16/12* (2006.01)
*A61M 16/10* (2006.01)
(Continued)

(52) U.S. Cl.
CPC ...... *A61M 16/125* (2014.02); *A61M 16/0066* (2013.01); *A61M 16/024* (2017.08);
(Continued)

(58) Field of Classification Search
CPC .............. A61M 16/00; A61M 16/0057; A61M 16/0063; A61M 16/0066; A61M 16/0069;
(Continued)

(56) References Cited

U.S. PATENT DOCUMENTS

| 3,605,785 A | 9/1971 | Dobritz |
| 4,141,354 A | 2/1979 | Ismach |

(Continued)

FOREIGN PATENT DOCUMENTS

| CA | 2201698 A1 | 10/1998 |
| EP | 482261 | 4/1992 |

(Continued)

OTHER PUBLICATIONS

International Search Report for International Application No. PCT/US2021/026579 dated Jul. 16, 2021 (3 pages).
(Continued)

*Primary Examiner* — Joseph D. Boecker

(57) ABSTRACT

The present disclosure relates generally to medical devices and, more particularly, to a gas mixing system for a medical ventilator. A gas mixer is provided to adjust the oxygen concentration of environmental air for a blower-based ventilator, by adjusting the mix of air upstream of the ventilator and providing the mixed air to the ventilator's environmental air inlet.

19 Claims, 14 Drawing Sheets

(51) Int. Cl.
*A61M 16/20* (2006.01)
*A61M 16/00* (2006.01)
*A61M 16/08* (2006.01)

(52) U.S. Cl.
CPC .... *A61M 16/0816* (2013.01); *A61M 16/1005* (2014.02); *A61M 16/12* (2013.01); *A61M 16/201* (2014.02); *A61M 16/203* (2014.02); *A61M 2016/0027* (2013.01); *A61M 2016/0039* (2013.01); *A61M 2016/1025* (2013.01); *A61M 2202/0208* (2013.01); *A61M 2205/502* (2013.01)

(58) Field of Classification Search
CPC ............ A61M 16/024; A61M 16/0816; A61M 16/1005; A61M 16/101; A61M 16/12; A61M 16/125; A61M 16/203; A61M 16/204; A61M 2016/0027; A61M 2016/1025

See application file for complete search history.

(56) References Cited

U.S. PATENT DOCUMENTS

| | | |
|---|---|---|
| 4,267,827 A | 5/1981 | Rauscher et al. |
| 4,340,044 A | 7/1982 | Levy et al. |
| 4,560,519 A | 12/1985 | Cerny |
| 4,602,653 A | 7/1986 | Ruiz-Vela et al. |
| 4,775,795 A | 10/1988 | Biehl et al. |
| 4,905,685 A | 3/1990 | Olsson et al. |
| 5,014,694 A * | 5/1991 | DeVries ............ A61M 16/12 128/205.24 |
| 5,044,362 A | 9/1991 | Younes |
| 5,092,326 A | 3/1992 | Winn et al. |
| 5,159,924 A | 11/1992 | Cegielski et al. |
| 5,186,167 A | 2/1993 | Kolobow |
| 5,237,987 A | 8/1993 | Anderson et al. |
| 5,255,675 A | 10/1993 | Kolobow |
| 5,299,568 A | 4/1994 | Forare et al. |
| 5,299,579 A | 4/1994 | Gedeon et al. |
| 5,383,449 A | 1/1995 | Forare et al. |
| RE34,938 E | 5/1995 | Serikov et al. |
| 5,452,714 A | 9/1995 | Anderson et al. |
| 5,522,381 A | 6/1996 | Olsson et al. |
| 5,664,560 A | 9/1997 | Merrick et al. |
| 5,676,133 A | 10/1997 | Hickle et al. |
| 5,692,497 A | 12/1997 | Schnitzer et al. |
| 5,722,392 A | 3/1998 | Skimming et al. |
| 5,722,449 A | 3/1998 | Heinonen et al. |
| 5,765,558 A | 6/1998 | Psaros et al. |
| 5,823,186 A | 10/1998 | Rossen et al. |
| 5,887,611 A | 3/1999 | Lampotang et al. |
| 5,915,834 A | 6/1999 | McCulloh |
| 5,934,274 A | 8/1999 | Merrick et al. |
| 5,954,051 A | 9/1999 | Heinonen et al. |
| 6,015,388 A | 1/2000 | Sackner et al. |
| 6,029,660 A | 2/2000 | Calluaud et al. |
| 6,076,523 A | 6/2000 | Jones et al. |
| 6,116,240 A | 9/2000 | Merrick et al. |
| 6,148,816 A | 11/2000 | Heinonen et al. |
| 6,158,434 A | 12/2000 | Lugtigheid et al. |
| 6,250,302 B1 | 6/2001 | Rantala |
| 6,279,574 B1 | 8/2001 | Richardson et al. |
| 6,390,988 B1 | 5/2002 | Robinson |
| 6,412,483 B1 | 7/2002 | Jones et al. |
| 6,467,478 B1 | 10/2002 | Merrick et al. |
| 6,659,961 B2 | 12/2003 | Robinson |
| 6,782,888 B1 | 8/2004 | Friberg et al. |
| 6,827,084 B2 | 12/2004 | Grubb, Jr. |
| 6,830,048 B2 | 12/2004 | Wruck et al. |
| 6,851,426 B1 | 2/2005 | Strömberg |
| 6,990,977 B1 | 1/2006 | Calluaud et al. |
| 7,219,666 B2 | 5/2007 | Friberg et al. |
| 7,275,540 B2 | 10/2007 | Bolam et al. |
| 7,509,957 B2 | 3/2009 | Duquette et al. |
| 7,516,742 B2 | 4/2009 | Stenzler et al. |
| 7,530,353 B2 | 5/2009 | Choncholas et al. |
| 7,610,914 B2 | 11/2009 | Bolam et al. |
| 7,779,834 B2 | 8/2010 | Calluaud et al. |
| 7,886,740 B2 | 2/2011 | Thomas et al. |
| 10,226,591 B1 * | 3/2019 | Tarler ................. A61M 16/022 |
| 2001/0022181 A1 | 9/2001 | Masson et al. |
| 2004/0200477 A1 | 10/2004 | Bleys et al. |
| 2005/0000517 A1 | 1/2005 | Eriksson et al. |
| 2006/0084931 A1 * | 4/2006 | Huang ................. A61M 16/10 604/317 |
| 2006/0231098 A1 | 10/2006 | Downie et al. |
| 2006/0249153 A1 * | 11/2006 | DeVries ............. F04C 29/0035 128/205.24 |
| 2007/0125374 A1 | 6/2007 | Smith et al. |
| 2007/0125377 A1 | 6/2007 | Heinonen et al. |
| 2007/0144523 A1 | 6/2007 | Bolam et al. |
| 2007/0169779 A1 | 7/2007 | Freeman |
| 2007/0181126 A1 | 8/2007 | Tolmie et al. |
| 2008/0078389 A1 | 4/2008 | Xiao et al. |
| 2008/0121233 A1 | 5/2008 | von Blumenthal et al. |
| 2008/0127975 A1 | 6/2008 | Lirsch et al. |
| 2008/0149104 A1 | 6/2008 | Eifler |
| 2008/0156328 A1 | 7/2008 | Taube |
| 2013/0239968 A1 * | 9/2013 | Friberg ............. A61M 16/0066 128/204.23 |
| 2021/0316104 A1 * | 10/2021 | Novkov ............. A61M 16/1005 |
| 2023/0166070 A1 * | 6/2023 | Wood .................. A61M 16/20 128/204.21 |

FOREIGN PATENT DOCUMENTS

| | | |
|---|---|---|
| WO | 9107912 | 6/1991 |
| WO | 9731670 | 9/1997 |
| WO | 9818383 | 5/1998 |
| WO | 74757 | 12/2000 |
| WO | 2011/078944 A1 | 6/2011 |
| WO | 2014/151804 A1 | 9/2014 |

OTHER PUBLICATIONS

International Written Opinion for International Application No. PCT/US2021/026579 dated Jul. 16, 2021 (6 pages).
7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Puritan Bennett 980 Series Ventilator Operator's Manual, Covidien, Jan. 29, 2014, Part. No. 10077893 A Jan. 2014, 506 pages.

* cited by examiner

GAS MIXING SYSTEM FOR MEDICAL VENTILATOR

CROSS-REFERENCE TO RELATED APPLICATIONS

This application claims the benefit of U.S. Provisional Application No. 63/008,508, filed Apr. 10, 2020, and U.S. Provisional Application No. 63/079,518, filed Sep. 17, 2020, the complete disclosures of which are hereby incorporated herein by reference in their entireties.

INTRODUCTION

Medical ventilator systems are used to provide ventilatory support to patients in hospitals, nursing facilities, surgery centers, and other clinical environments. Some ventilators include blowers that generate pressurized air to provide to the patients. Depending on the particular condition of a patient, ambient air is enriched with oxygen and the mixture of air is provided to the patient. The oxygen concentration that is desired to be delivered to the patient may depend on the particular patient or condition of the patient.

These ventilators connect to a patient through a breathing hose (often called a circuit) that has an inspiratory limb and expiratory limb. Inhalation gases flow from the ventilator to the patient through the inspiratory limb, and exhalation gases from the patient back to the ventilator through the expiratory limb. At the patient, the breathing circuit connects to a patient interface such as a mask, nasal cannula, endotracheal tube, or tracheostomy tube.

It is with respect to these and other general considerations that the aspects disclosed herein have been made. Also, although relatively specific problems may be discussed, it should be understood that the examples should not be limited to solving the specific problems identified in the background or elsewhere in this disclosure.

SUMMARY

Examples of the present disclosure describe systems and methods for increasing oxygen concentrations for medical ventilators. In an aspect, the technology relates to a system for increasing oxygen concentration. The system includes an oxygen valve configured to be coupled to an oxygen source; an oxygen plenum coupled to the valve; and a mixing valve. The mixing valve includes an oxygen inlet coupled to the oxygen plenum; an ambient-air inlet; and an outlet configured to be attached to an inlet of a blower of a ventilator. In an example, the oxygen valve is a proportional valve. In another example, the mixing valve is one of a manual mixing valve or an electromechanical mixing valve controlled by a signal from a microprocessor based on a user setpoint. In yet another example, the system further includes a dial to control the mixing valve, wherein different settings of the dial correspond to different oxygen concentrations provided at the outlet of the mixing valve. In still another example, the system further includes a pressure sensor coupled to the oxygen plenum. In a further example, the pressure sensor is configured to measure a differential pressure between gas in the oxygen plenum and ambient air.

In another example, the system further includes a control device, the control device configured to perform a set of operations that include receiving the differential pressure measured by the pressure sensor; and based on the measured differential pressure, generating a control signal to control the oxygen valve to maintain a target pressure of gas within the oxygen plenum. In a yet another example, the measured differential pressure is below the target pressure; and the control signal is configured to open the oxygen valve. In still yet another example, the measured differential pressure is above the target pressure; and the control signal is configured to close the oxygen valve.

In another example, the target pressure is less than or equal to 0.5 inH2O. In a further example, the ambient-air inlet of the mixing valve further includes a check valve to prevent flow of oxygen from the oxygen plenum through the ambient-air inlet. In yet another example, the system further includes at least one of a check valve or a relief valve coupled to the oxygen plenum to relieve gas pressure in the oxygen plenum.

In another aspect, the technology relates to a system for increasing oxygen concentration. The system includes an oxygen valve configured to be coupled to an oxygen source, an oxygen plenum coupled to the valve, and a mixing valve. The mixing valve includes an oxygen inlet coupled to the oxygen plenum; an ambient-air inlet; and an outlet configured to be attached to an inlet of a blower of a ventilator. The system further includes a pressure sensor coupled to the oxygen plenum. The pressure sensor is configured to measure a differential pressure between gas in the oxygen plenum and ambient air. The system also includes a control device communicatively coupled to the pressure sensor and the oxygen valve. The control device is configured to perform a set of operations. The operations include receiving the differential pressure measured by the pressure sensor; and based on the measured differential pressure, generating a control signal to control the oxygen valve to maintain a target pressure of gas within the oxygen plenum.

In an example, the measured differential pressure is below the target pressure; and the control signal is configured to open the oxygen valve. In another example, the measured differential pressure is above the target pressure; and the control signal is configured to close the oxygen valve. In yet another example, the target pressure is less than or equal to 0.5 inH2O.

In another aspect, the technology relates to a method for increasing oxygen concentration. The method includes measuring, by a pressure sensor, a first differential pressure between ambient air and gas in an oxygen plenum; based on the first differential pressure, generating, by a control device, a first control signal; transmitting the first control signal to an oxygen valve to cause the oxygen valve to change position to affect flow of oxygen into the oxygen plenum; measuring, by the pressure sensor, a second differential pressure between the ambient air and gas in the oxygen plenum; based on the second differential pressure, generating, by a control device, a second control signal; and transmitting the second control signal to the oxygen valve to cause the oxygen valve to change position to affect flow of oxygen into the oxygen plenum.

In an example, generating the first control signal is further based on a comparison of the first differential pressure and a target pressure; and generating the second control signal is further based on a comparison of the second differential pressure and the target pressure. In another example, the target pressure is less than or equal to 0.5 inH2O. In yet another example, the first differential pressure is less than the target pressure and the first control signal is configured to cause the oxygen valve to open. In still another example, the second differential pressure is greater than the target pressure and the second control signal is configured to cause the oxygen valve to close. In a further example, the method also includes altering a setting of a mixing valve, coupled to the oxygen plenum, to alter an oxygen concentration provided from the mixing valve.

In an aspect, the technology relates to a medical ventilator system including a ventilator comprising a first environmental gas inlet, an inspiratory port, an expiratory port, and a blower, wherein the blower is located in a gas flow path between the first environmental gas inlet and the inspiratory port. The system also includes an oxygen regulator comprising an oxygen inlet, a second environmental gas inlet, a mixing valve, and a mixed gas outlet, wherein the mixing valve combines oxygen from the oxygen inlet and gas from the second environmental gas inlet into a mixed gas provided to the mixed gas outlet. The system further includes a fluidic coupling between the ventilator and the oxygen regulator for coupling the mixed gas outlet of the oxygen regulator to the first environmental gas inlet of the ventilator.

In an example, the blower is operable to apply a negative pressure to the first environmental gas inlet of the ventilator, and wherein the negative pressure is applied to the mixed gas outlet of the oxygen regulator via the fluidic coupling. In another example, the negative pressure is further applied to the second environmental gas inlet of the oxygen regulator via the mixing valve. In yet another example, the oxygen regulator further comprises a plenum upstream of the mixing valve, and a pressure regulating valve between the plenum and the oxygen inlet. In still another example, the oxygen regulator comprises a housing having a knob or hardware input coupled to the mixing valve to adjust the mixing valve. In a further example, the ventilator comprises an interface that mounts to the oxygen regulator. In still yet another example, the oxygen regulator comprises a rigid casing comprising a hollow plenum between the oxygen inlet and the mixing valve.

In another aspect, the technology relates to a gas regulator for retrofitting a blower-based medical ventilator. The gas regulator includes a housing comprising a compressed gas inlet, an environmental gas inlet, and a mixed gas outlet. The gas regulator also includes a plenum defined by the housing; a mixing valve between the plenum and the mixed gas outlet; a pressure-regulating valve between the plenum and the compressed gas inlet; and a controller operatively coupled to the pressure-regulating valve.

In an example, gas regulator further includes a pressure sensor measuring a pressure of compressed gas inside the plenum. In another example, the controller receives the measured pressure from the pressure sensor. In a further example, the controller is programmed to adjust the pressure-regulating valve upon determining that the measured pressure is less than threshold. In yet another example, the gas regulator further includes a user-adjustable hardware input mechanically coupled to the mixing valve.

In another aspect, the technology relates to a method for regulating breathing gases for a blower-based medical ventilator. The method includes mixing room air and oxygen at a first ratio to form a first breathing gas in a gas flow path upstream of the blower-based ventilator; introducing the first breathing gas to an inlet of the blower-based medical ventilator; pressurizing the first breathing gas inside the blower-based medical ventilator and providing the pressurized first breathing gas to an inspiratory port of the blower-based medical ventilator; upstream from the blower-based ventilator, adjusting the first ratio to a second ratio that is different from the first ratio; and mixing room air and oxygen at the second ratio to form a second breathing gas, and introducing the second breathing gas to the inlet of the blower-based medical ventilator. In an example, introducing the first breathing gas to the inlet of the blower-based medical ventilator comprises connecting an outlet of a gas regulator to the inlet of the blower-based medical ventilator.

In another aspect, the technology relates to a method of configuring a medical ventilator. The method includes providing a gas regulator comprising an oxygen inlet, an air inlet, a mixing valve, and a mixed gas outlet; fluidically coupling a source of compressed oxygen gas to the oxygen inlet of the gas regulator; and fluidically coupling the mixed gas outlet of the gas regulator to an environmental gas inlet of the medical ventilator. The method further includes operating the mixing valve to combine the compressed oxygen gas with air from the air inlet at a first ratio, to form a mixed gas; and providing the mixed gas to the environmental gas inlet of the medical ventilator.

In an example, the ventilator includes a high-pressure oxygen inlet, and the method further includes closing the high-pressure oxygen inlet of the ventilator. In another example, the method further includes adjusting, inside the gas regulator, a pressure of the compressed oxygen gas from a first pressure and providing the mixed gas at a second pressure that is different from the first pressure. In a further example, the second pressure that is lower than the first pressure. In yet another example, the method further includes adjusting a pressure of the mixed gas within the ventilator to a third pressure different from the second pressure, and providing the pressurized mixed gas to an inspiratory port of the ventilator for delivery to a patient. In still another example, the third pressure is higher than the second pressure. In still yet another example, the method further includes measuring a percent concentration of oxygen (FiO2) in the mixed gas or the pressurized mixed gas, and adjusting the mixing valve according to the measured FiO2. In another example, the method includes de-coupling the mixed gas outlet of the gas regulator from the environmental gas inlet of the medical ventilator, and operating the medical ventilator independently of the gas regulator.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Additional aspects, features, and/or advantages of examples will be set forth in part in the description which follows and, in part, will be apparent from the description, or may be learned by practice of the disclosure.

BRIEF DESCRIPTION OF THE DRAWINGS

Non-limiting and non-exhaustive examples are described with reference to the following figures.

DETAILED DESCRIPTION

As discussed above, some ventilators include a blower that provides ambient air into a ventilator and ultimately to a patient. Some of these ventilators may also include an input to receive low-pressure concentrated oxygen. Such ventilators, however, may be limited in the amount of oxygen concentration that can be provided to a patient. For example, oxygen concentration that is delivered to the patient may be limited to ranges near 50% or lower. The lower oxygen concentration may not be appropriate for treating patients that have conditions that are best treated with higher oxygen concentrations, such as 95% and higher. Accordingly, an improvement to ventilators to improve oxygen concentrations is desired.

Among other benefits, the present technology provides solutions to increasing oxygen concentration in ventilators having blowers. The present technology enriches the air at the inlet of the blower with additional oxygen. Thus, when the blower is initiated, the air that is propelled by the blower has a higher concentration of oxygen, resulting in a higher concentration of oxygen ultimately provided to the patient. To provide oxygen-enriched air at the blower, the present technology may actively control pressure of an oxygen-filled plenum. The gas within the plenum is then be provided to the inlet of a blower via a mixing valve. The mixing valve may be used to set the oxygen concentration that is desired to be provided to the inlet of the blower. By actively controlling the pressure of gas in the plenum, the pressure of gas provided at the inlet of blower may be maintained to be greater than ambient pressure. In addition, the pressure of the gas in the plenum may be maintained at a level where substantial oxygen is not exhausted into the ambient air and neither the blower nor the ventilator controls are significantly affected by the gas provided from the plenum.

Figure 1:
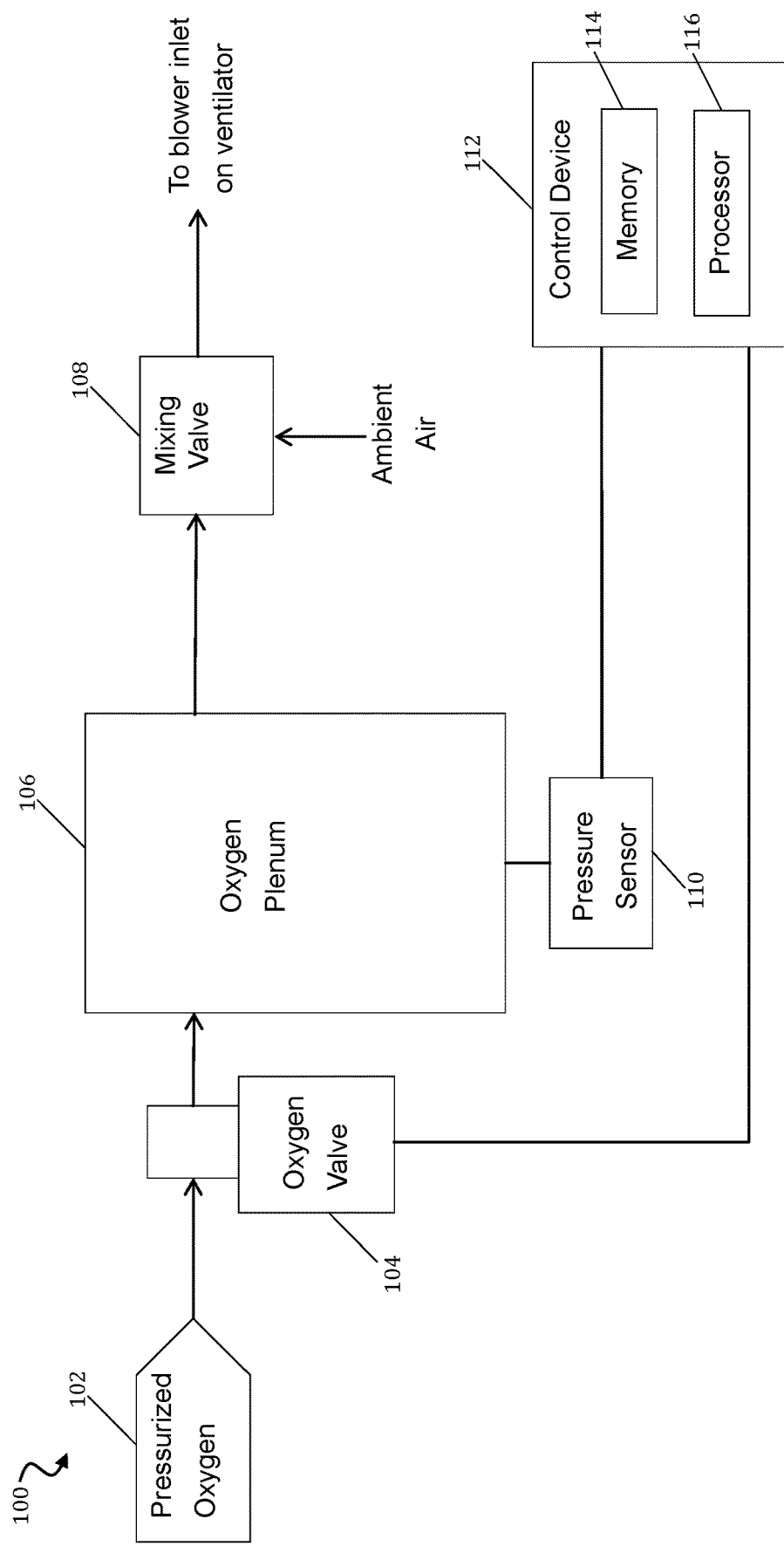
FIG. 1 depicts an example system for increasing oxygen concentration.

FIG. 1 depicts an example system 100 for increasing oxygen concentration. The system 100 may be attached or coupled to an inlet of a blower of a ventilator to increase the oxygen concentration that can be provided by the ventilator. The system 100 includes an oxygen plenum 106 that is filled or pressurized from a pressurized oxygen source 102. The flow of oxygen from the oxygen source 102 is controlled by an oxygen valve 104. The valve 104 may be any valve suitable for controlling the flow of a gas. In some examples, the valve 104 may be a proportional solenoid (PSOL) valve where the amount of flow may be proportionally regulated. In other examples, the valve 104 may be a valve that is either fully open or fully closed.

The pressure of the gas in the plenum 106 may be controlled by a control loop that includes at least a pressure sensor 110 and a control device 112. The pressure sensor 110 may measure the pressure of the gas in the plenum 106. The measure of the pressure of the gas may be relative to the ambient pressure, such as a differential pressure between ambient air and the gas in the plenum. A certain pressure for the gas in the plenum 106 may be targeted. For example, the targeted pressure may be less than about 1.0 inH$_2$O (2.52 cmH$_2$O) above the ambient pressure. In some instances, the targeted pressure for the gas in the plenum 106 may be less than or equal to about 0.5 inH$_2$O (1.27 cmH$_2$O) or less than or equal to about 0.2 inH$_2$O (0.5 cmH$_2$O). Accordingly, the targeted pressure is not substantially higher than the ambient air. The intent of the target pressure is maintain a slight pressure of gas from plenum 106 at the inlet of the blower. By maintaining a slight pressure, rather than a high pressure, a minimal amount of oxygen is wasted by being exhausted into the ambient air. In addition, high pressure gas may have a negative effect on the blower or operation of the ventilator. For example, if a high pressure gas is applied to the blower, the gas that is ultimately provided to the patient may be provided at too high a pressure and/or the control algorithms of the ventilator may malfunction due to the high pressure gas provided at the inlet of the blower. With the slight pressure increase of the present technology, the blower and ventilator are substantially unaffected with the exception of being able to deliver a higher oxygen concentration.

In some examples, the targeted pressure may also be slightly less than ambient pressure. In such examples, the oxygen valve 104 opens only to charge the plenum 106 when a slightly negative pressure, caused by blower inlet vacuum, is sensed. For example, when the blower is activated, gas is drawn from the plenum 106 and may create a pressure within the plenum 106 that is less than the ambient pressure. In examples, where a slightly negative pressure triggers opening of the oxygen valve 104, a check valve may be included downstream of the plenum 106 and upstream of the mixing valve 108. The check valve prevents the flow of ambient air backwards through the mixing valve 108 and into the slight vacuum that exists in the plenum 106. For example, the targeted pressure may be between about 0.0 to −0.1 inH$_2$O or 0.0 to −0.2 inH$_2$O. Other target pressures may be used. When a breath is being delivered by the ventilator causing the blower to ramp up in speed, the pressure at the blower inlet is a slight vacuum of perhaps 1 inH$_2$O. The pressure sensor 110 detects that the pressure in the plenum 106 is below the target pressure, and the control device 112 sends a signal to the oxygen valve 104 to open, which charges the plenum 106.

The control loop includes a control device 112. The control device 112 receives pressure measurements, from the pressure sensor 110, of the pressure of gas in the plenum 106. Based on the pressure measurements received from the pressure sensor 110, the control device 112 generates a control signal to change the position of the valve 104. For example, if the gas pressure drops below the targeted pressure, the control device 112 generates a control signal to open the valve to allow more oxygen to flow into the plenum 106. In contrast, if the gas pressure increases above the targeted pressure, the control device 112 generates a control signal to close the valve to reduce or cease the flow of oxygen into the plenum 106 from the oxygen source 102.

The control device 112 is communicatively coupled to the valve 104 to allow for control signals generated from the control device 112 to be sent to the valve 104.

In examples where valve 104 is a PSOL valve or other proportional valve where the position of the valve 104 may be set between fully open and fully closed positions, the control signal from the control device 112 may cause the valve 104 to open or close in amount less than the full range of the valve 104. In examples, where the valve 104 is either fully open or fully closed, the control signal from the control device 112 may cause the valve 104 to fully open or fully close. For such two-position valves that are either fully open or fully closed, a hysteresis loop may be implemented to prevent constant or rapid switching between states. In such examples, the hysteresis band may be about 0.1 in$H_2O$ or 0.05 in$H_2O$ around the targeted pressure of the gas in the plenum 106. Accordingly, no matter the type of valve 104 used, the valve 104 may be controlled by the control device 112 to maintain a targeted pressure of gas within the oxygen plenum. In some examples, control loop is relatively fast, and the control device 112 may process pressure measurements and generate valve control signals one every millisecond or faster.

In some implementations, a proportional valve, such as a PSOL, may be preferable to allow for more accurate control of the pressure in the plenum 106. In addition, the use of a proportional valve help prevents rapid full closings and openings of the valve 104, which may cause metal components of valve to impact one other with a large amount of force. Such impacts may be disfavored in an oxygen-rich environment.

The control device 112 may include a memory 114 and at least one processor 116. For example, the memory 114 may store instructions that, when executed by the processor 116, causes the control device 112 to perform the operations described herein. In some examples, the control device 112 may be a miniature computer or microcontroller, such as an ARDUINO NANO microcontroller available from the Arduino AG or Somerville, Massachusetts. In other examples, the control device 112 may be an integrated circuit (IC), programmable logic device (PLD), or a field-programmable gate array (FPGA), among other possible configurations or implementations. The control loop may also be a proportional-integral-derivative (PID) loop and control device 112 may be a PID controller.

The mixing valve 108 may be used to mix the oxygen from the plenum 106 with ambient air to achieve a desired oxygen concentration. The mixing valve 108 may include a first inlet to receive oxygen from the plenum 106 and a second inlet that is open to ambient air. The mixing valve 108 causes the oxygen from the plenum 106 to mix with ambient air, and the mixing valve 108 provides the gas mixture through at outlet that is configured to be coupled to a blower inlet of a ventilator. As an example, a dial may be connected to the mixing valve 108 that allows for various oxygen concentration levels to be selected or set. By moving the dial to increase the oxygen concentration level, the mixing valve is adjusted to increase the flow of oxygen from the plenum 106 as compared to the flow of ambient air. Such an adjustment may be achieved by altering the area of an aperture coupling the plenum 106 to output of the mixing valve 108 as compared an area of an aperture coupling the ambient air to the output of the mixing valve 108. In some examples, the mixing valve 108 may be controlled electronically based on a desired oxygen concentration level. The desired oxygen concentration level may be received as a signal from the ventilator, the control device 112, or another device that is capable of receiving a desired oxygen concentration level as an input and generate a signal corresponding to that concentration level to control the mixing valve 108.

In operation, when the system is connected to a blower of ventilator, the blower may initiate to provide a breath to a patient connected to the ventilator. The blower may include a fan that spins for a duration and speed based on the characteristics of the breath to be delivered to the patient, such as tidal volume, pressure targets, flow targets, etc. When the blower is activated, the gas mixture from the mixing valve 108 drawn through the inlet of the blower. When the gas mixture is drawn through the mixing valve 108, the pressure of gas in the plenum 206 decreases. The decrease in pressure is measured by the pressure sensor 110, and the corresponding pressure measurement is provided to the control device 112. The control device 112 then generates a control signal to cause the valve 104 to open, at least partially, to allow oxygen to flow from the oxygen source 102 into the plenum 106 to raise the pressure.

Of note, the system 100 may be compatible with blowers that are rated to handle the maximum oxygen concentration, such as 100% oxygen, that is to be provided by the system 100 to the blower. If the blower is not rated to handle oxygen-rich inputs, risk of combustion may increase.

Figure 2:
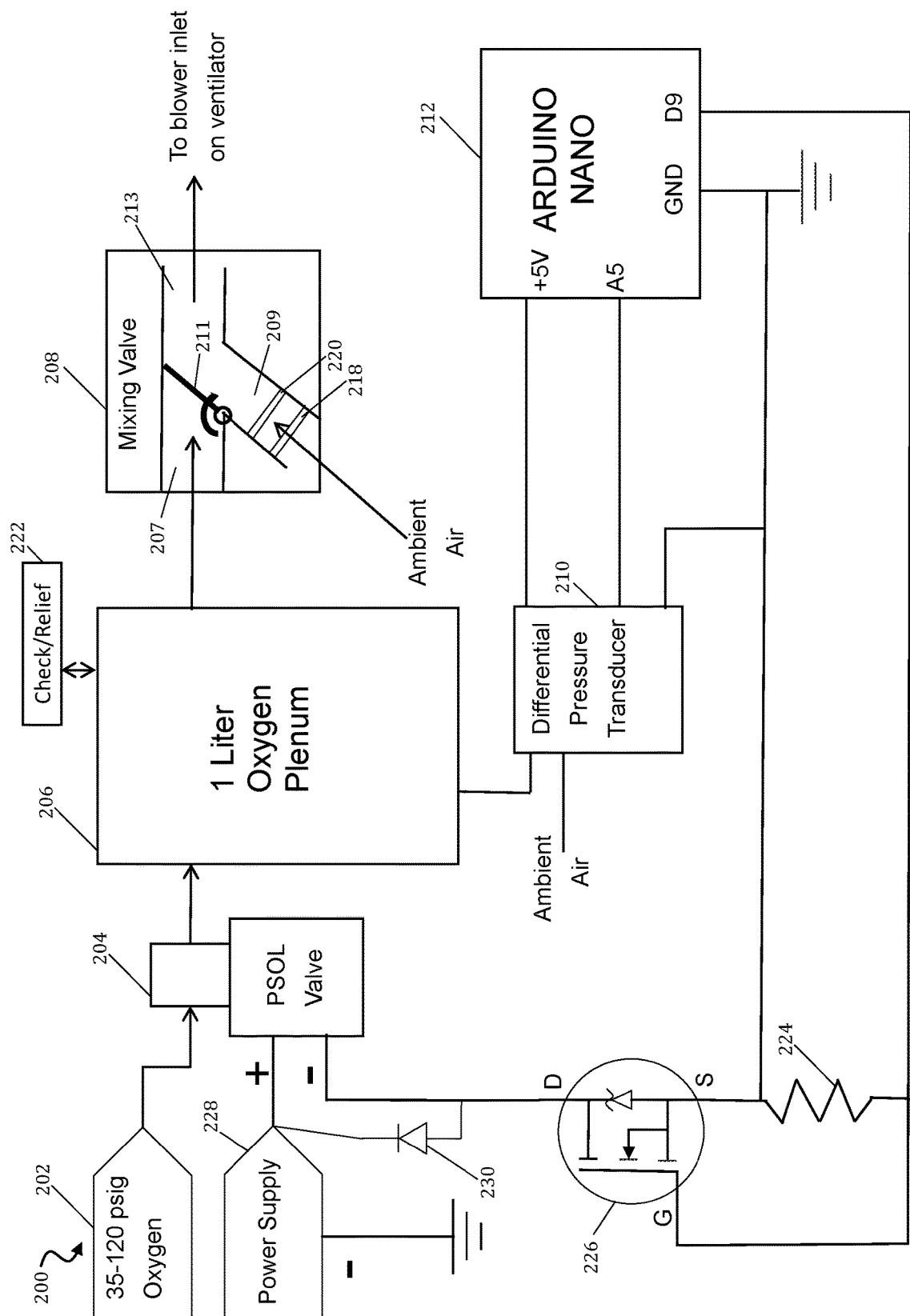
FIG. 2 depicts another example system for increasing oxygen concentration.

FIG. 2 depicts another example system 200 for increasing oxygen concentration. System 200 is a specific example implementation of the system 100 discussed above and depicted in FIG. 1. System 200 includes PSOL valve 204 that controls the flow of oxygen from an oxygen source 202 to an oxygen plenum 206. The oxygen source 202 may provide oxygen at a pressure between 35-120 pounds per square inch gauge (psig). A regulator may also be incorporated into, or connected to, the oxygen source 202 to regulate the pressure provided by the oxygen source 202. In examples where a proportional valve is used, such as PSOL valve 204, a regulator may not be necessary because the PSOL valve 204 may be set to have a small or large opening to account for a wide variety of input pressures from the oxygen source 202. The PSOL valve may be powered by a power supply 228. In the example depicted, the positive terminal of the power supply is connected to the PSOL valve 204 and the negative terminal of the power supply is connected to ground.

The oxygen plenum 206 in the example may have a volume of about one liter, but the volume of the plenum 206 may change in different examples. The size of the plenum 206 may be based on the tidal volumes that are to be provided by the ventilator. The size of the plenum 206 may also be based on the pressure available from the oxygen source 202. In some examples, it may be desirable to maintain a saturation of the plenum 206 with oxygen, and the plenum 206 may be sized accordingly.

An outlet of the plenum 206 is coupled to an oxygen inlet 207 of a mixing valve 208. The mixing valve 208 also includes an ambient-air inlet 209 that is open to ambient air. The mixing valve 208 also includes an outlet 213 to provide a mixture of gas to a blower inlet of a ventilator. The mixing valve 208 in the example depicted in FIG. 2 is a manual mixing valve. The mixture of oxygen from the oxygen inlet 207 and ambient air from the ambient-air inlet 209 may be controlled by rotating a valve member 211, which may be a "flapper." By rotating the valve member 211, the area of the aperture between inlet 207 and outlet 213 is altered at the same time as the area of the aperture between inlet 209 and outlet 213. Accordingly, the mixture of oxygen and ambient air (e.g., the oxygen concentration of the gas mixture) that is provided through the outlet 213 may be adjusted by rotating the valve member 211. In some examples, the valve member 211 may be manually rotated by a rotating a dial. The dial may have a plurality of settings that correspond to the oxygen concentration of the gas mixture provided at the outlet 213 of the mixing valve 208. Each setting of the dial causes the valve member 211 to be positioned such that the mixing valve 208 provides the set oxygen concentration. The mixing valve 208 may also be of the "spool valve" type, where the linear action of a shaft moves a spool across the ports of a 3-port valve to achieve the same mixing function.

In some examples, the ambient-air inlet 209 may also include an air filter 218 to filter the ambient air. The ambient-air inlet 209 may also include a check valve 220 that prevents the flow of oxygen from the plenum 206 through the ambient-air inlet 209. In some examples, the check valve 220 may be omitted. Even with the check valve 220 omitted, the amount of oxygen that flows out of the ambient-air inlet 209 is limited due to the relatively small pressure differential between the gas in the plenum 206 and ambient air. In examples where the check valve 220 is included, a check and/or relief valve 222 may also be connected to the plenum 206 to prevent over-pressurization or under-pressurization of the plenum 206. Over-pressurization of oxygen may introduce undesired hazards, impact the control algorithms of the ventilator, and/or impact the pressure, flow, and/or tidal volume of the breath delivered to the patient. In some examples, the check and/or relief valve 222 may be set to relieve any gas pressure above 5 cmH$_2$O in the plenum 206 over ambient air pressure. Similarly, the check and/or relief valve 222 may be set to allow gas to flow into the plenum 206 if the pressure of the gas in the plenum 206 is less than 5 cmH$_2$O below ambient air pressure.

The system 200 also includes a differential pressure transducer 210. The differential pressure transducer measures a differential pressure between the pressure of the ambient air and the pressure of the gas in the plenum 206. The transducer 210 includes an input for ambient air, which may be a port open to ambient air. The transducer 210 also includes an input that is pneumatically coupled to the plenum 206 to allow for the pressure differential to be measured by the transducer 210. The measured differential pressure between the ambient air and the gas in the plenum 206 is provided from the transducer 210 to a control device 212. As a specific example, the transducer 210 may be a P993 pressure sensor available from Sensata Technologies of Attleboro, Massachusetts.

In the example depicted, the control device 212 is an ARDUINO NANO. The transducer 210 may be connected to the +5V pin and an input pin, such as the A5 pin, of the control device 212. The transducer 210 and the control device 212 may also be connected to a common ground. The control device 212 operates as discussed above. For example, based on the measured differential pressure, a control signal is generated to either cause the PSOL valve 204 to move towards a closed position or an open position. To provide the control signal to the PSOL valve, an output of the control device, such as output in D9 of the ARDUINO NANO, may be coupled to a gate (G) of a transistor 226. The drain (D) of the transistor 226 is then coupled to the negative terminal of the PSOL valve 204, and the source (S) of the transistor 226 is connected to ground. The transistor 226 may be an N-channel MOSFET. As a specific example, the transistor may be a STD12NF06L-1 Power MOSFET available from STMicroelectronics of Geneva, Switzerland. The source (S) and gate (G) may also be connected by a resistor 224. In a specific example, the resistor may have a resistance of 56 kΩ. A recovery diode or rectifier 230 may be included between the positive and negative inputs of the PSOL valve 204. In a specific example, the rectifier 230 may be a 1N4005 recovery diode available from ON Semiconductor of Phoenix, Arizona.

Figure 3:
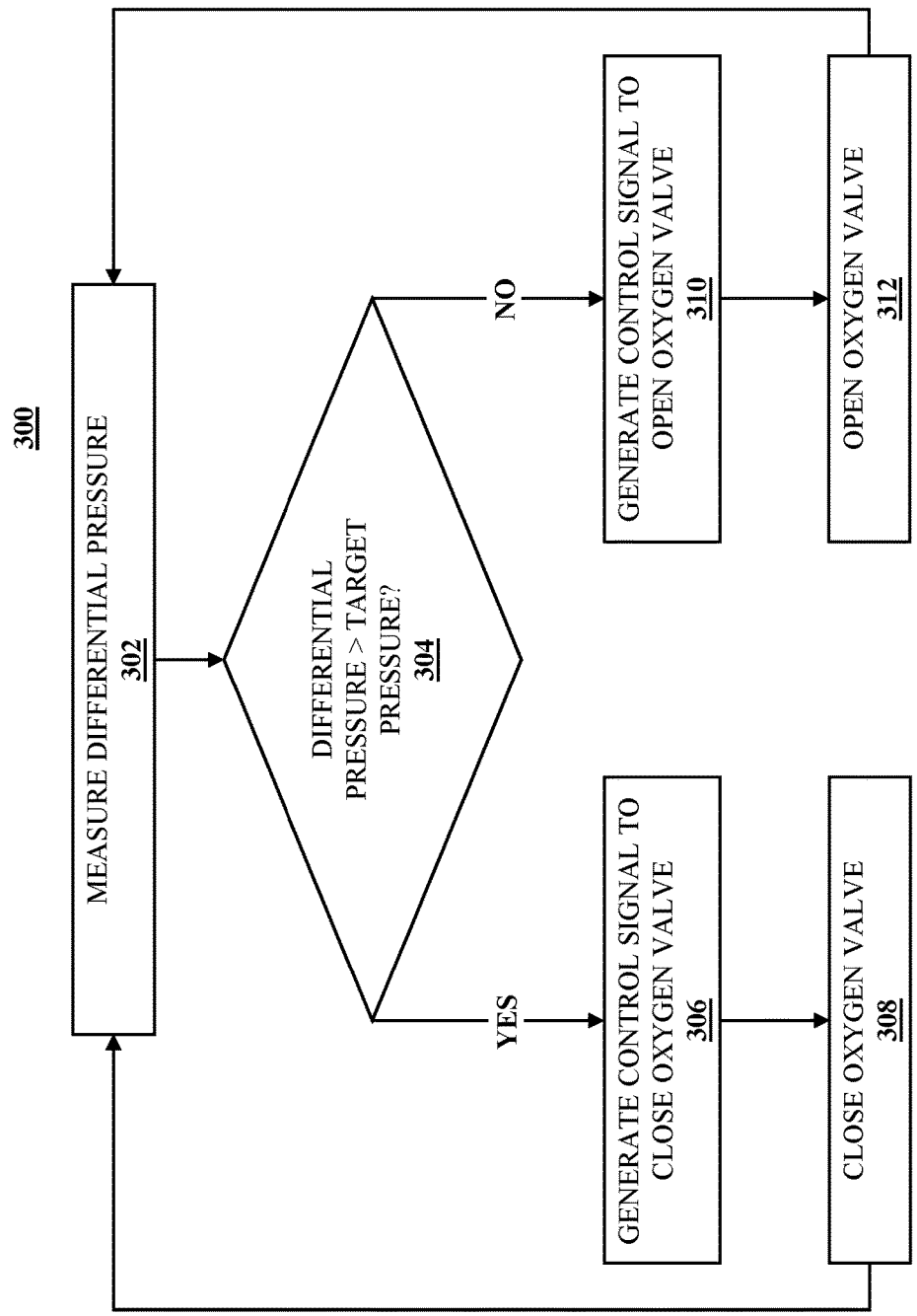
FIG. 3 depicts an example method for increasing oxygen concentration.

FIG. 3 depicts an example method 300 for increasing oxygen concentration to be provided to a blower inlet of a ventilator. At operation 302, a differential pressure between ambient air and gas inside the oxygen plenum is measured. The differential pressure may be measured by a pressure sensor. At operation 304, a determination is made as to whether the measured differential pressure is greater than a target pressure for the gas in the oxygen plenum. The determination may be made by a control device. If the differential pressure is determined to be greater than the target pressure in operation 304, method 300 flows to operation 306 where the control device generates a control signal to close the oxygen valve that controls flow of oxygen from the oxygen source into the oxygen plenum. The control signal may be configured to entirely close the valve or partially close the oxygen valve. At operation 308, the oxygen valve receives the control signal and closes according to the control signal. After operation 308, method 300 flows back to operation 302 where the method 300 repeats.

If the differential pressure is determined to not be greater than the target pressure in operation 304, method 300 flows to operation 310 where the control device generates a control signal to open the oxygen valve. At operation 312, the oxygen valve receives the control signal and opens according to the control signal. After operation 308, method 300 flows back to operation 302 where the method 300 repeats.

Figure 4:
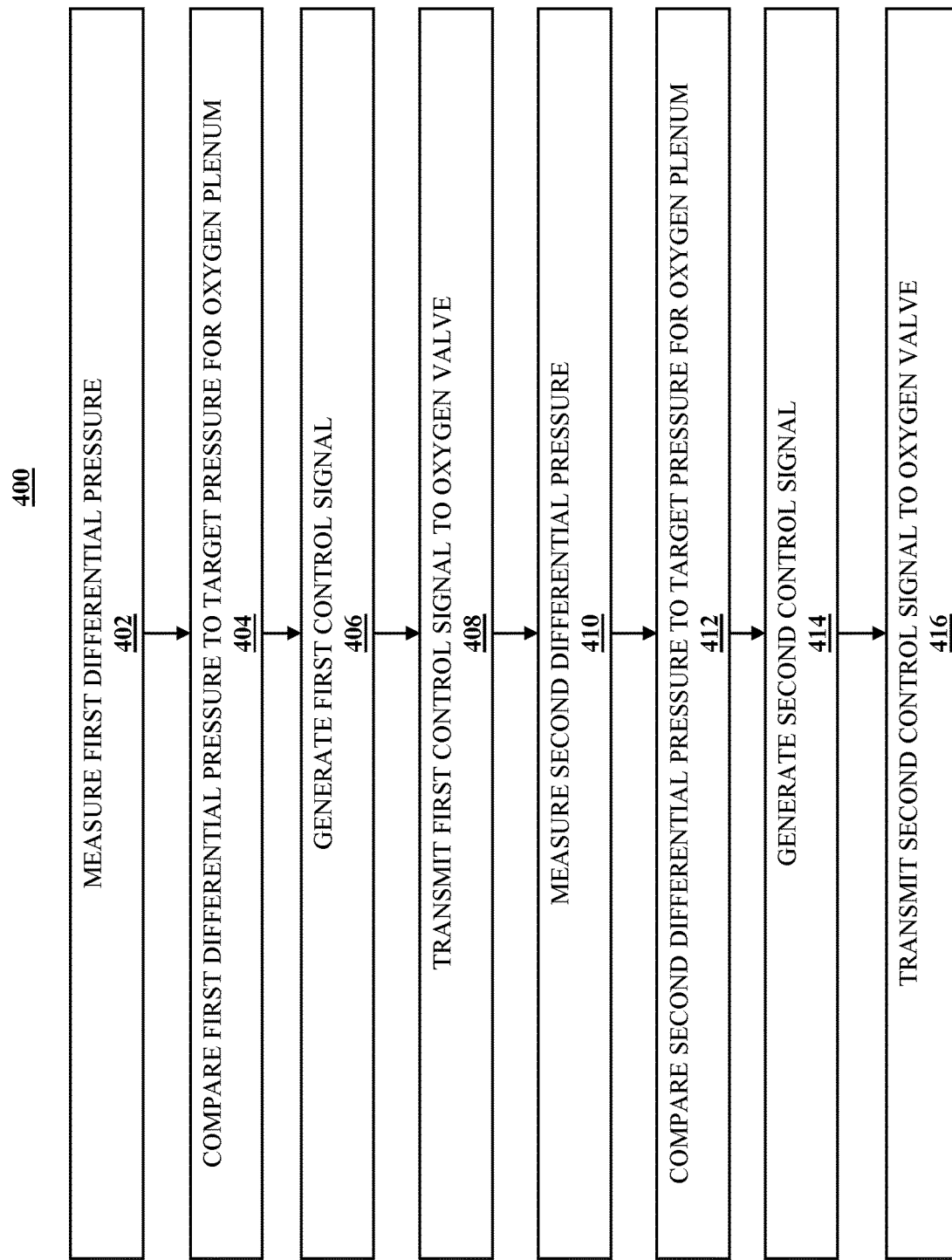
FIG. 4 depicts another example method for increasing oxygen concentration.

FIG. 4 depicts another example method 400 for increasing oxygen concentration to be provided to a blower inlet of a ventilator. At operation 402, a first differential pressure between ambient air and gas in an oxygen plenum is measured by a pressure sensor. At operation 404, the measured first differential pressure is compared, by a control device, to a target pressure for the oxygen plenum. At operation 406, a first control signal for an oxygen valve is generated by the control device. Generation of the first control signal is based on the first differential pressure and/or the comparison performed in operation 404. At operation 408, the first control signal is transmitted to the oxygen valve to cause the oxygen valve to change position to affect flow of oxygen into the oxygen plenum. As an example, if the comparison in operation 404 indicates that the first differential pressure is less than the target pressure, the first control signal is configured to cause the oxygen valve to open.

At operation 410 a second differential pressure between ambient air and gas in an oxygen plenum is measured by the pressure sensor. The second differential pressure may be measured immediately after the first differential pressure measurement or at a substantial time (e.g., greater than 5 seconds) after the first differential pressure measurement. Accordingly, additional differential pressure measurements may, or may not, occur between the first pressure differential measurement and the second pressure differential measurement. At operation 412, the measured second differential pressure is compared, by the control device, to the target pressure for the oxygen plenum. At operation 414, a second control signal is generated by the control device. Generation of the second control signal is based on the second differential pressure and/or the comparison performed in operation 412. At operation 416, the second control signal is transmitted to the oxygen valve to cause the oxygen valve to change position to affect flow of oxygen into the oxygen plenum.

Figure 5:
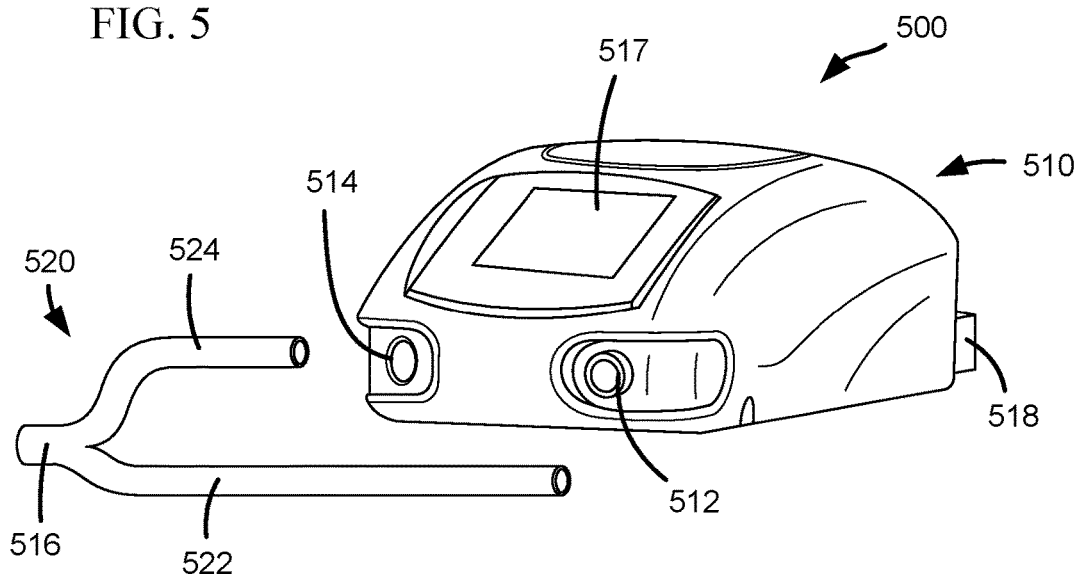
FIG. 5 is a perspective view of a ventilator system according to an embodiment of the present disclosure.

A medical ventilator system 500 is shown in FIG. 5, according to an embodiment. The system 500 includes a ventilator 510 and a dual-limb breathing circuit 520. The ventilator 510 includes an inspiratory port 512, expiratory port 514, and display screen 517. The breathing circuit 520 includes an inspiratory limb 522 that carries breathing gases from the inspiratory port 512 to a patient, and an expiratory limb 524 that carries exhaled gases from the patient to the expiratory port 514. The two limbs 522, 524 are connected by a wye 516, which in turn connects to a patient interface such as a mask, endotracheal tube, or other airway interface applied to the patient.

Medical ventilators supply pressurized breathing gases, at pressures above atmospheric pressure, at the inspiratory port to deliver gas into the patient's lungs. The increased pressure in the inspiratory breathing gas can come from a high pressure source external to the ventilator (such as pressurized gas in wall outlets at medical facilities, or pressurized gas canisters, bottles, or tanks) or from pressure applied by components on-board the ventilator (such as an on-board compressor or blower). In the latter case, the ventilator draws in environmental air, such as room air, and pressurizes the air before providing it to the inspiratory port to deliver to a patient.

In an embodiment, a medical ventilator system includes a ventilator with a first environmental gas inlet, an inspiratory port, an expiratory port, and a blower. The blower is located in a gas flow path between the first environmental gas inlet and the inspiratory port. The system also includes an oxygen regulator having an oxygen inlet, a second environmental gas inlet, a mixing valve, and a mixed gas outlet. The mixing valve combines oxygen from the oxygen inlet and gas from the second environmental gas inlet into a mixed gas provided to the mixed gas outlet. The system also includes a fluidic coupling between the ventilator and the oxygen regulator for coupling the mixed gas outlet of the oxygen regulator to the first environmental gas inlet of the ventilator.

In an embodiment, the ventilator 510 is a blower-based ventilator that supplies pressurized breathing gases to the inspiratory port 512 from environmental air, such as room air. As shown in FIG. 5, the ventilator 510 includes an environmental gas inlet 518. A blower inside the ventilator draws room air into the ventilator through the gas inlet 518, pressurizes the air, and supplies the pressurized air to the inspiratory port 512. The environmental gas inlet 518 takes in air at a pressure that is at or about atmospheric pressure.

According to an embodiment, a gas mixer or regulator is provided to adjust the oxygen concentration of environmental air for a blower-based ventilator, by adjusting the mix of air upstream of the ventilator and providing the mixed air to the ventilator's environmental air inlet. In this way, the ventilator can operate independently of the gas regulator, with or without the gas regulator. When the gas regulator is used, it provides additional capability to adjust and control the composition of breathing gases delivered by the blower-based ventilator.

Figure 6A:
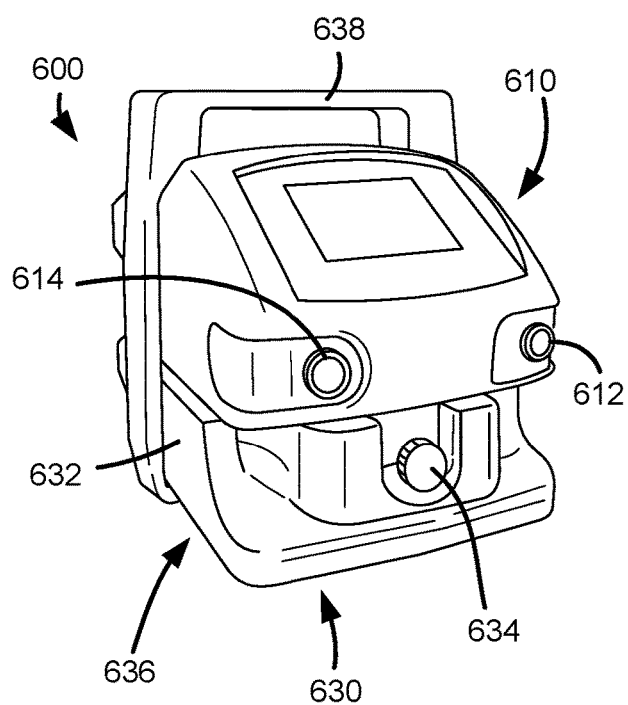
FIG. 6A is a perspective view of a ventilator system according to an embodiment of the present disclosure.
Figure 6B:
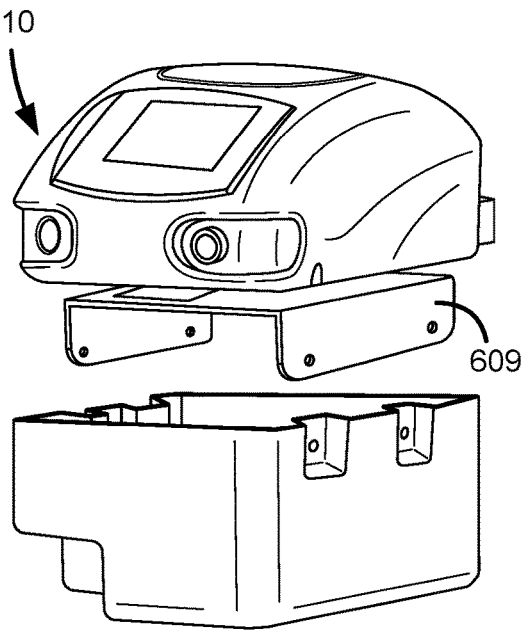
FIG. 6B is an exploded view of a ventilator and gas regulator according to an embodiment of the present disclosure.

FIG. 6A shows an embodiment of a system 600 including a ventilator 610 and a gas (such as oxygen) regulator 630. The ventilator 610 includes an inspiratory port 612 and an expiratory port 614. The gas regulator includes a housing 632 and a user-adjustable knob 634 (or other hardware input such as a button, handle, dial, lever, or similar mechanism) for controlling the regulator. In the embodiment shown, the housing 632 is shaped as a base 636 for the ventilator, which is mounted to the base 636 by attaching a bottom surface of the ventilator to a top surface of the base. The base 636 also includes a handle 638 for carrying the combined unit. Optionally, the gas regulator can be mounted to the ventilator via an interface such as a mating surface or an attachment plate 609, as shown in FIG. 6B. The plate 609 mounts to the bottom of the ventilator, and to the top of the regulator.

Figure 7:
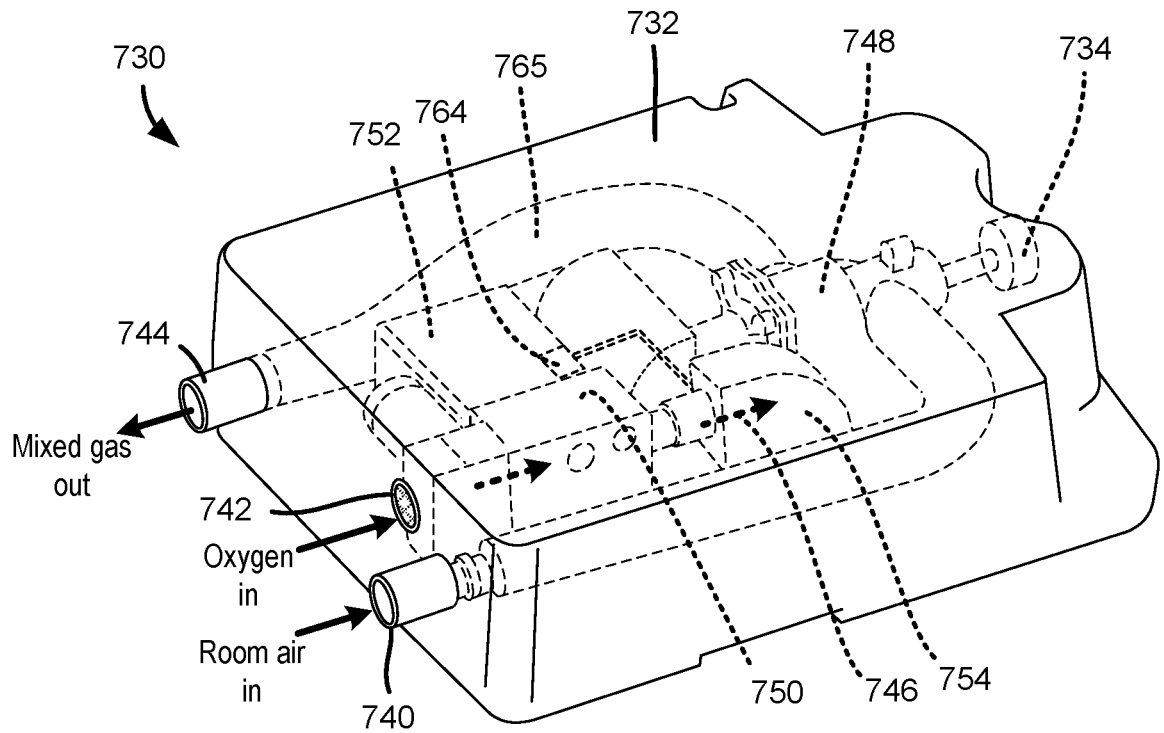
FIG. 7 is a perspective internal view of a gas regulator according to an embodiment of the present disclosure.

FIG. 7 shows a perspective view of an oxygen regulator 730 with an outer housing 732, according to an embodiment. The housing 732 is depicted as transparent in FIG. 7 in order to show the internal components of the regulator 730. The regulator 730 includes an environmental air inlet 740, an oxygen inlet 742, and a mixed air outlet 744. The mixed air outlet 744 is coupled to the gas inlet of the ventilator (such as gas inlet 518 in FIG. 5) to provide the regulated, mixed gas from the regulator into the ventilator. In FIG. 7, oxygen gas enters the regulator at the oxygen inlet 742, such as by connecting an oxygen tank, bottle, canister, or flow line to the oxygen inlet 742. The oxygen flows through the regulator through oxygen flow path 746 to a mixing valve 748. Environmental air, such as room air, enters the regulator at the inlet 740 and flows to the mixing valve 748. The mixing valve 748 mixes the environmental air and oxygen to a desired ratio of oxygen to air—the fractional percent of inspired oxygen (FiO2)—and delivers mixed gas at the FiO2 ratio to the mixed gas outlet 744 via conduit 765.

In an embodiment, the user can adjust the FiO2 by adjusting the knob 734, which turns the mixing valve 748 to allow relatively more or less oxygen into the mix. In an embodiment, the mixing valve 748 is a globe valve. The globe valve is controlled purely mechanically, and provides a substantially linear response to rotation of the knob 734. Other types of gas mixing valves, including automatic valves that, for example, are software-controlled, may also be suitable.

In an embodiment, the gas regulator 730 receives oxygen at the oxygen inlet 742 at relatively high pressure compared to the atmospheric pressure at the room air inlet 740. For example, the gas regulator 730 can receive compressed oxygen from medical gas sources such as wall outlets at a hospital, which may provide oxygen at a pressure of 35-80 psi. The gas regulator 730 regulates and reduces this pressure to provide mixed gas at the outlet 744 at a lower pressure, such as at or near atmospheric pressure, such as 0-2 (zero to two) $cmH_2O$ differential gage pressure above atmospheric pressure (as an example, 0.25 $cmH_2O$ differential gage pressure). One advantage of this pressure regulation is that the mixed gas outlet 744 may be connected to the environmental gas inlet of the ventilator, which may be designed to interface with atmospheric pressure. This may allow an embodiment of the oxygen regulator to be used with existing ventilators without requiring substantial modifications to the ventilator. Thus, the gas regulator intercepts the high-pressure oxygen, mixes it with air at a desired FiO2 ratio, and then delivers the mixed gas to the ventilator at or near atmospheric pressure.

In an embodiment, a pressure-regulating valve is provided in the oxygen flow path 746 to regulate and reduce the pressure of the incoming oxygen gas. In the embodiment shown in FIG. 7, the pressure-regulating valve is a proportional solenoid valve (PSOL) 750, which is in-line in the flow path between the oxygen inlet 742 and the mixing valve 748. The PSOL 750 is operated by a controller 752 that opens and closes the PSOL 750 to achieve a targeted pressure, such as a pressure at or just above the local atmospheric pressure. The oxygen gas exits the PSOL 750 and enters an oxygen reservoir 754, such as an open space or plenum defined by the housing 732. The oxygen collects in this reservoir 754 at a pressure at or near or just above atmospheric pressure. The oxygen can be drawn from the reservoir 754 into the mixing valve 748, where it intersects with the atmospheric air from the air inlet 740 to form the mixed gas, which is provided to the mixed gas outlet 744 downstream of the mixing valve.

Figure 8:
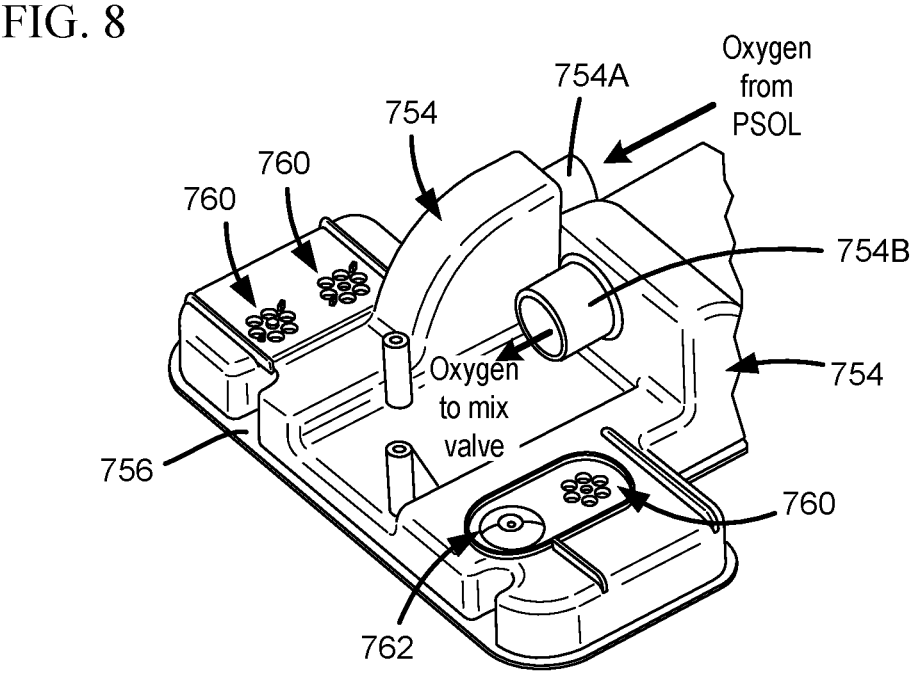
FIG. 8 is a partial perspective view of components of a gas regulator according to an embodiment of the present disclosure.

Another view of the oxygen flow path and plenum is shown in FIG. 8. In this embodiment, the oxygen reservoir 754 is formed as an open space or plenum inside a hollow molding 756. The molding 756 sits inside the housing 732 of the regulator. As shown in FIG. 8, the molding 756 is formed with an inlet 754A and an outlet 754B. The inlet 754A connects to the exit of the PSOL 750. The outlet 754B connects to the inlet of the globe valve 748. Thus, the oxygen flow path 746 passes from the oxygen inlet 742, through the PSOL 750, through the reservoir inlet 754A into the reservoir 754, through the reservoir outlet 754B, and into the mixing valve 748. In this embodiment, the molding 756 is formed with one or more pressure relief valves for safety, such as one or more vacuum relief valves and one or more high pressure relief valves. In the example shown, the molding 756 has three vacuum relief valves 760 and one high pressure relief valve 762. The vacuum relief valves 760 open when a vacuum of sufficient amount is present inside the reservoir 754, to open the reservoir 754 to the atmosphere and allow air to be drawn into the reservoir 754 and into the flow path to the ventilator. This is a safety mechanism to allow air to enter the ventilator in case the regulator malfunctions (such as the PSOL 750 locks in a closed position), to enable the patient to continue to breathe. The high pressure relief valve(s) 762 opens in the opposite scenario, when a high pressure of sufficient amount builds up inside the reservoir 754. In this case, the valve 762 opens to release the high pressure to the atmosphere. This is a safety mechanism to allow air to exit the plenum in case the regulator malfunctions (such as PSOL 750 locks in an open position), to prevent over-pressurization of the patient circuit.

A pressure sensor 764 is provided to measure the pressure of the oxygen within the reservoir 754. The pressure sensor 764 can be located at any suitable point that can measure or sample the pressure of gas within the plenum or open space of the reservoir, such as the space inside the molding 756. In an embodiment, the pressure sensor 764 is mounted to or integrated with the controller 752, and connects to a pressure port in the reservoir 754 (shown in dotted lines in FIG. 7). In an embodiment, the pressure port is separated from the PSOL 750 to reduce the impact of the PSOL on the measurements at the pressure sensor. The oxygen exiting the PSOL 750 can be turbulent, and the pressure port is spaced apart from the PSOL 750 so that the pressure signal from the sensor 764 avoids some of the fluctuations from the turbulent gas at the PSOL exit. The measurement from the pressure sensor 764 is provided to the controller 752 to control the PSOL 750. When the pressure in the reservoir 754 drops below a threshold (such as a differential gage pressure, such as 0.25 cmH$_2$O above local atmospheric pressure), the controller 752 opens the PSOL 750 to refill the reservoir 754 until the threshold is reached again. This control cycle maintains a sufficient supply of oxygen inside the reservoir 754 to respond to breath demands from the ventilator. The reservoir 754 provides a supply of oxygen that is ready to be drawn into the mixing valve to deliver to the ventilator and to the patient. This ready supply of oxygen is available on demand when the ventilator or the patient initiates a new breath or a new inhalation cycle. When the oxygen is depleted, the pressure drops, the signal from the pressure sensor 764 registers that drop in pressure, and the controller responds by opening the PSOL to refill the reservoir. The PSOL acts to maintain the pressure in the reservoir at or just above atmospheric pressure. In an embodiment, the reservoir is sized to provide a volume of oxygen for at least one breath, such as 0.5, 1, 1.5, or 2 Liters. In an embodiment, the reservoir is smaller than the volume of oxygen for a single breath, and the gas regulator supplies the reservoir with oxygen at a rate greater than the rate of oxygen consumption by the ventilator.

In an embodiment, the regulator is designed to deliver the gas mixture at close to ambient pressure, as that is what the ventilator is designed to intake. By delivering air at or just above ambient pressure, the regulator does not build up excess pressure upstream of the ventilator (over-pressurizing the ventilator), or create a negative pressure vacuum upstream of the ventilator (throttling the ventilator, or adding excess resistance to the air supply to the ventilator). The ventilator is expecting low resistance at its inlet, as it expects to be drawing from an open source of environmental air (such as room air). The reservoir inside the gas regulator provides a volume that can respond to the inlet of the ventilator with low resistance.

Figure 9:
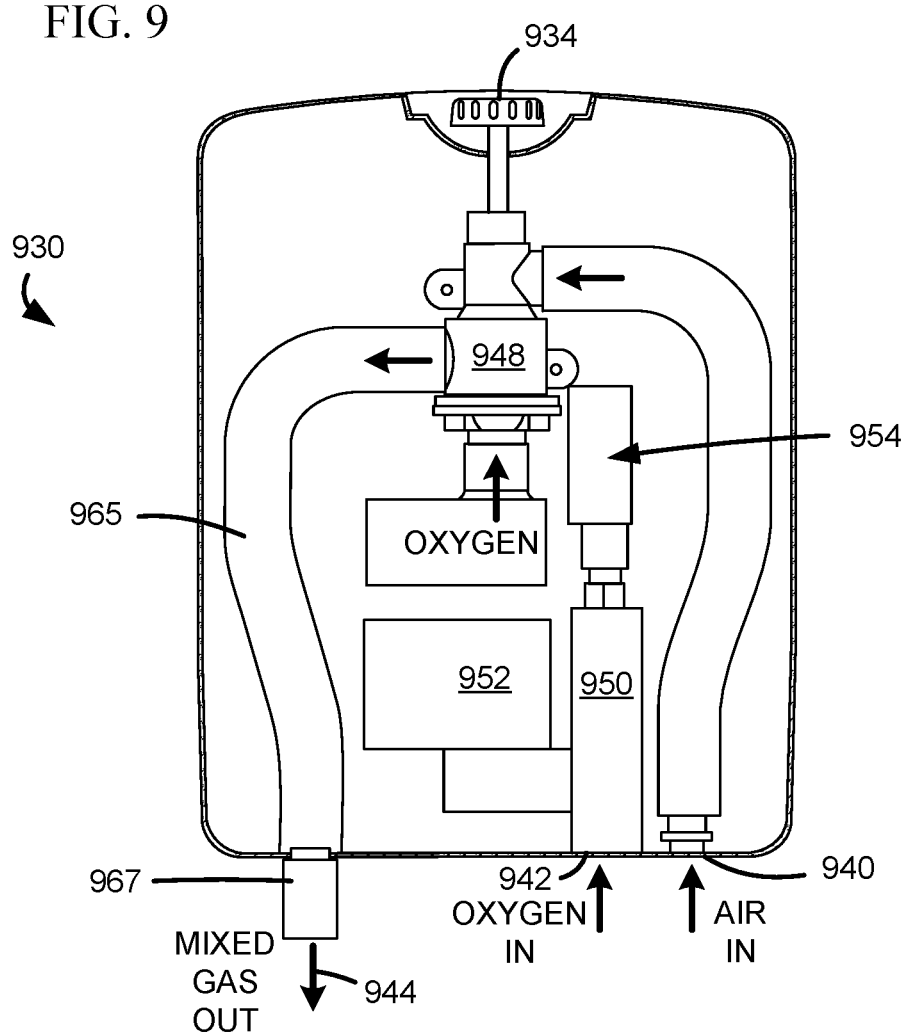
FIG. 9 is a top internal view of a gas regulator according to an embodiment of the present disclosure.
Figure 10:
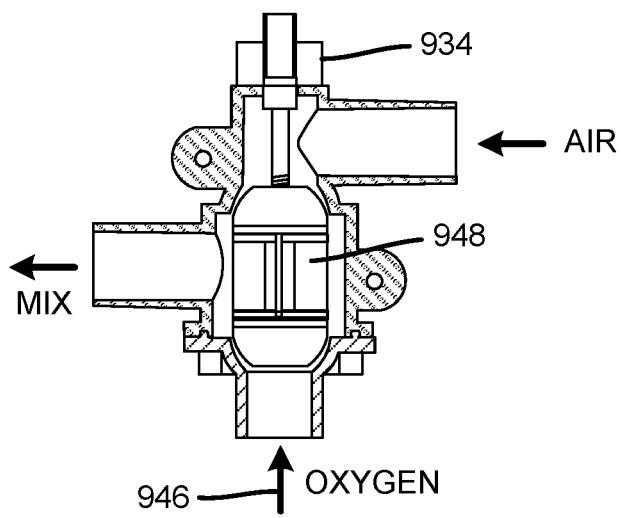
FIG. 10 is a side view of a mixing valve and gas flow paths according to an embodiment of the present disclosure.

A top view of the gas regulator is shown in FIG. 9, and a close-up view of the mixing valve is shown in FIG. 10. As seen in FIG. 9, the mixed gas exits the regulator 930 through a conduit 965 to a connector 967 at the exterior of the housing. In an embodiment, the connector 967 is a standard (15 mm or 22 mm) connector for airway interfaces. FIG. 9 also shows the room air inlet 940, the oxygen inlet 942, the gas outlet 944, the PSOL 950, the controller 952, and the reservoir 954. FIG. 10 shows the mechanical connection of the knob 934 to the mixing valve 948. FIG. 10 also shows the oxygen flow path 946.

Figure 11:
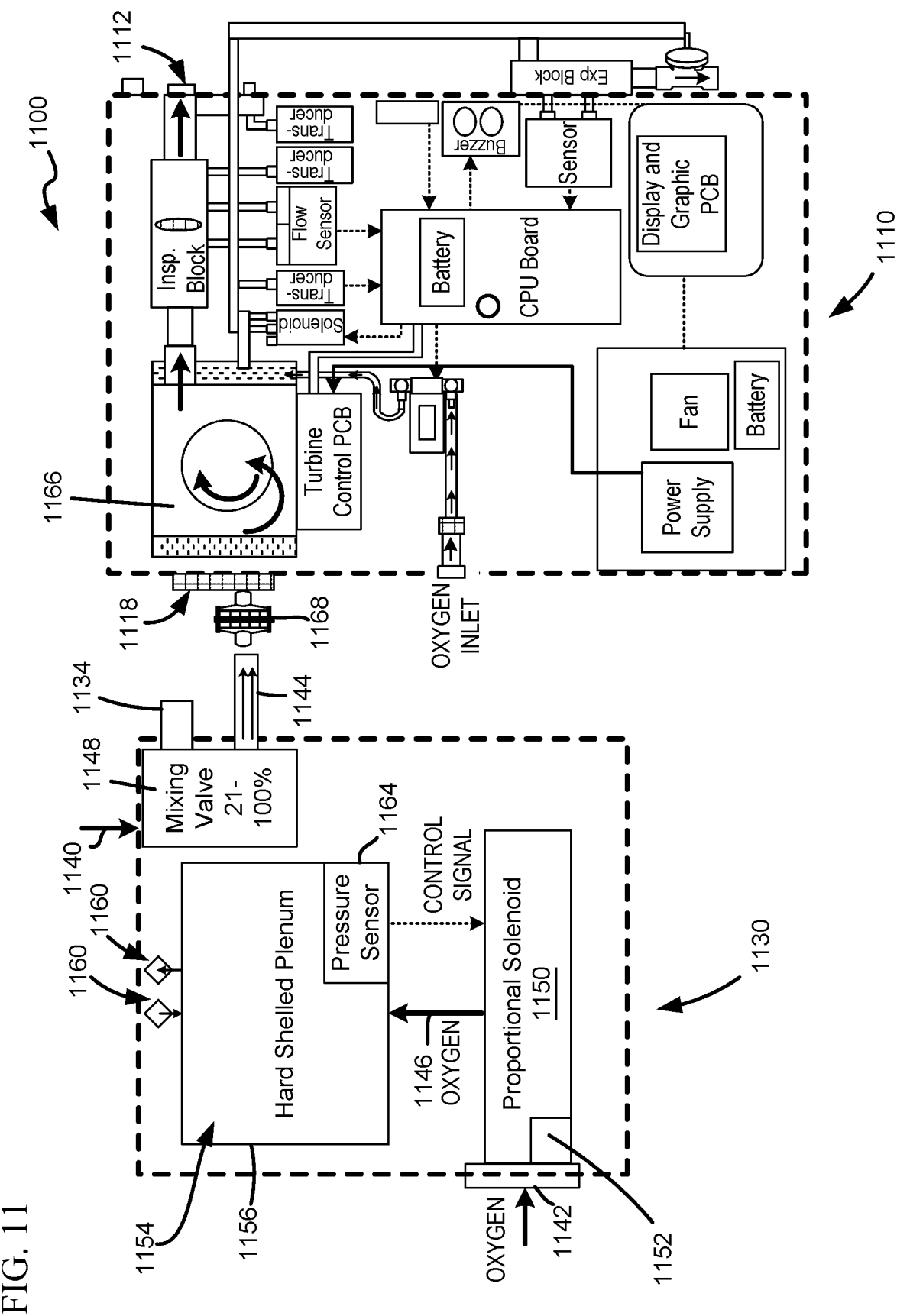
FIG. 11 is a block diagram view of a ventilation system according to an embodiment of the present disclosure.

A ventilation system 1100 including a blower-based ventilator 1110 and an oxygen regulator 1130 is shown in FIG. 11. The ventilator 1110 includes a blower or fan 1166 that generates pressure and flow from the environmental inlet 1118, in order to provide pressurized breathing gas to the inspiratory port 1112 at the front of the ventilator, which connects to the patient breathing circuit. The blower 1166 creates a negative pressure at the inlet 1118. As shown in FIG. 11, the oxygen regulator 1130 is connected to the ventilator 1110 by coupling the mixed gas outlet 1144 of the regulator to the inlet 1118 of the ventilator. A filter 1168 may be connected between the regulator and the ventilator. The mixed gas outlet 1144 is sealed against the ventilator inlet 1118, such as by a friction fit or suction seal between the conduits. The negative pressure generated by the blower is then applied to the mixed gas outlet of the regulator. This negative pressure propagates upstream toward the mixing valve 1148, where the negative pressure helps to draw air and oxygen into the mixing valve from environmental inlet 1140 and reservoir 1154, respectively.

In an embodiment, the regulator 1130 does not incorporate a blower, motor, compressor, or other component that applies pressure to a supply of gas. The regulator provides mixed gas at above-atmospheric pressure by accumulating pressure from the high-pressure O$_2$ line. The regulator can also rely on the negative pressure from the inlet of the ventilator to draw mixed gas from the regulator into the ventilator. As a result, no motor or blower is needed on board the regulator.

FIG. 11 shows the pressure sensor 1164 that measures a pressure of the oxygen inside the hard-shelled plenum or casing 1156, and the control signal that passes from the pressure sensor 1164 to the controller 1152 of the PSOL 1150. FIG. 11 also shows a knob 1134 for the mixing valve 1148, an oxygen inlet 1142, an oxygen flow path 1146, and relief valves 1160.

Figure 12:
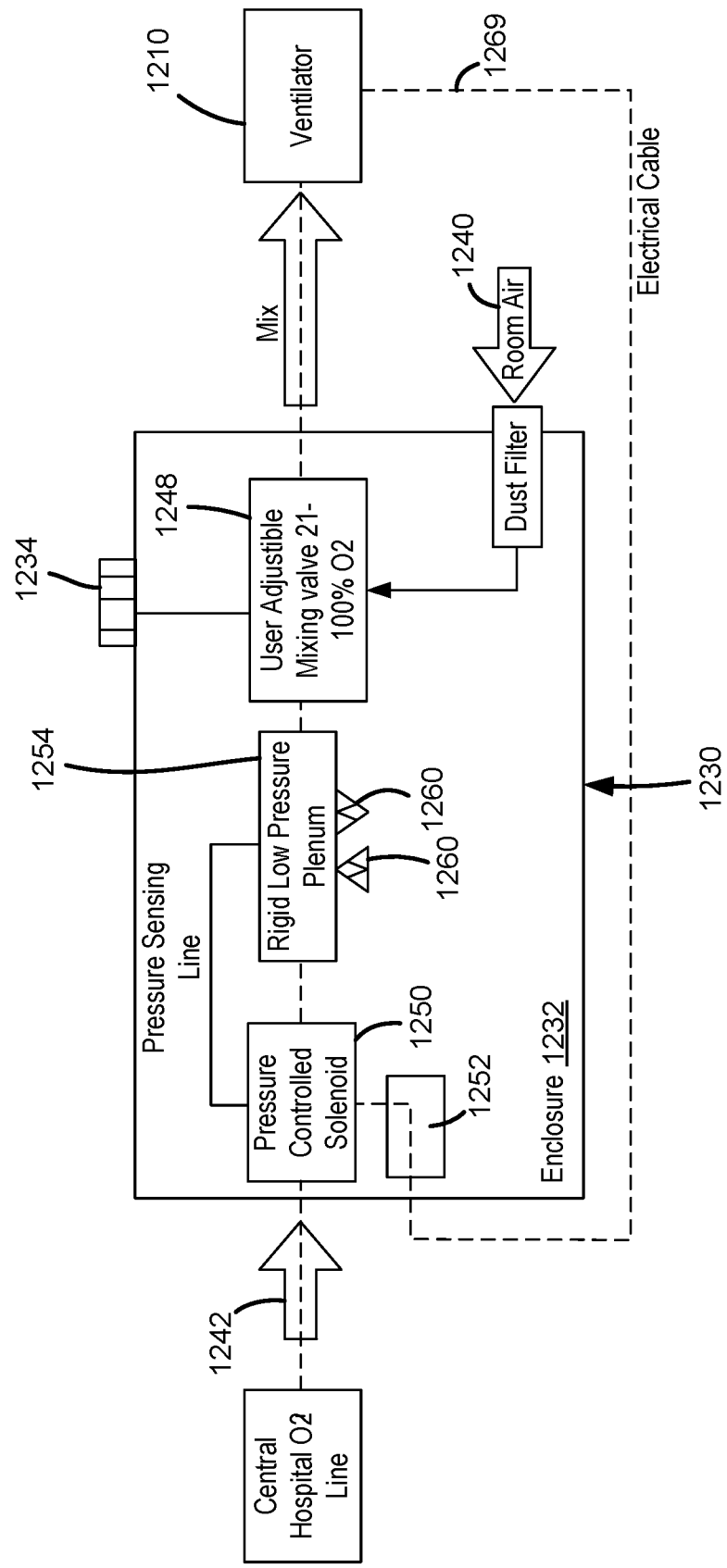
FIG. 12 is a block diagram view of a ventilation system according to an embodiment of the present disclosure.

Another block diagram is shown in FIG. 12, showing a ventilator 1210 connected to a gas regulator 1230. Optionally, an electrical cable 1269 connects the ventilator 1210 and the regulator 1230, for passing power and/or control signals between them. Optionally, the cable 1269 provides electrical power to the regulator from the ventilator, such as to power the PSOL 1250 and associated controller. Optionally, the cable 1269 provides signals from the ventilator to the regulator, such as a signal to shut the PSOL if the ventilator is malfunctioning (such as operating at too high a temperature, which can prevent a fire safety risk when connected to a source of pure oxygen). In an embodiment, a control signal to close the PSOL is sent from the ventilator (via cable 1269) to the regulator based on the temperature of the ventilator blower (such as a motor of the blower) exceeding a threshold. Signals exchanged between the regulator and ventilator can include measurements from the ventilator (system/component status, therapy values, or patient parameters), or any of the control signals that the ventilator uses to control ventilation. For example, the FiO2 measurement value may be sent from the ventilator to the gas regulator for purposes of automated globe valve control. In another embodiment, the control signal to the blower within the ventilator may be sent to the gas regulator so as to improve the response time of the gas regulator PSOL (for example, controlling the gas regulator PSOL to increase oxygen supply based on an increase in blower speed, and vice versa). FIG. 12 also shows the enclosure or housing 1232, the knob 1234, the room air inlet 1240, the oxygen inlet 1242, the mixing valve 1248, the controller 1252, the reservoir or plenum 1254, and the relief valves 1260.

Figure 13:
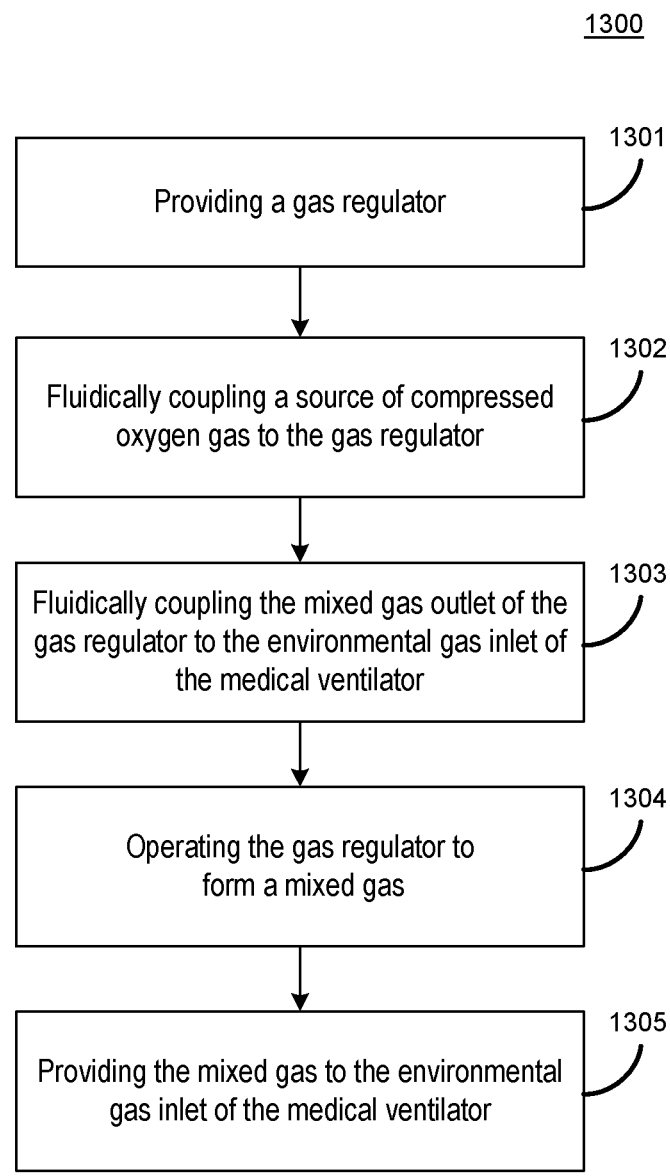
FIG. 13 is a flowchart of a method of configuring a medical ventilator having an environmental gas inlet, according to an embodiment of the present disclosure.

FIG. 13 shows a method 1300 of configuring a medical ventilator having an environmental gas inlet, according to an embodiment. The method includes providing a gas regulator (1301), and fluidically coupling a source of compressed oxygen gas to the gas regulator (1302). The gas regulator may have an oxygen inlet, a room air inlet, a mixing valve, and a mixed gas outlet, and the source of compressed oxygen gas is coupled to the oxygen inlet. The method includes fluidically coupling the mixed gas outlet of the gas regulator to the environmental gas inlet of the medical ventilator (1303), and operating the gas regulator to form a mixed gas (1304). This can be done by setting or adjusting the mixing valve to combine the compressed oxygen gas with air from the room air inlet at a first ratio. The method also includes providing the mixed gas to the environmental gas inlet of the medical ventilator (1305).

In an embodiment, the method 1300 includes adjusting, inside the gas regulator, a pressure of the compressed oxygen gas from a first pressure and providing the mixed gas at a second pressure that is different from (such as lower than) the first pressure; subsequently adjusting a pressure of the mixed gas within the ventilator to a third pressure different from (such as higher than) the second pressure; and providing the pressurized mixed gas to an inspiratory port of the ventilator for delivery to a patient. The room air entering the gas regulator can be pressurized air, for example if a plenum is provided upstream of the gas regulator. This may be useful in an environment where the room environment is dirty and contamination of the air supply is a concern, so room air is passed through a filtering and pressurizing step upstream of the gas regulator.

Figure 14:
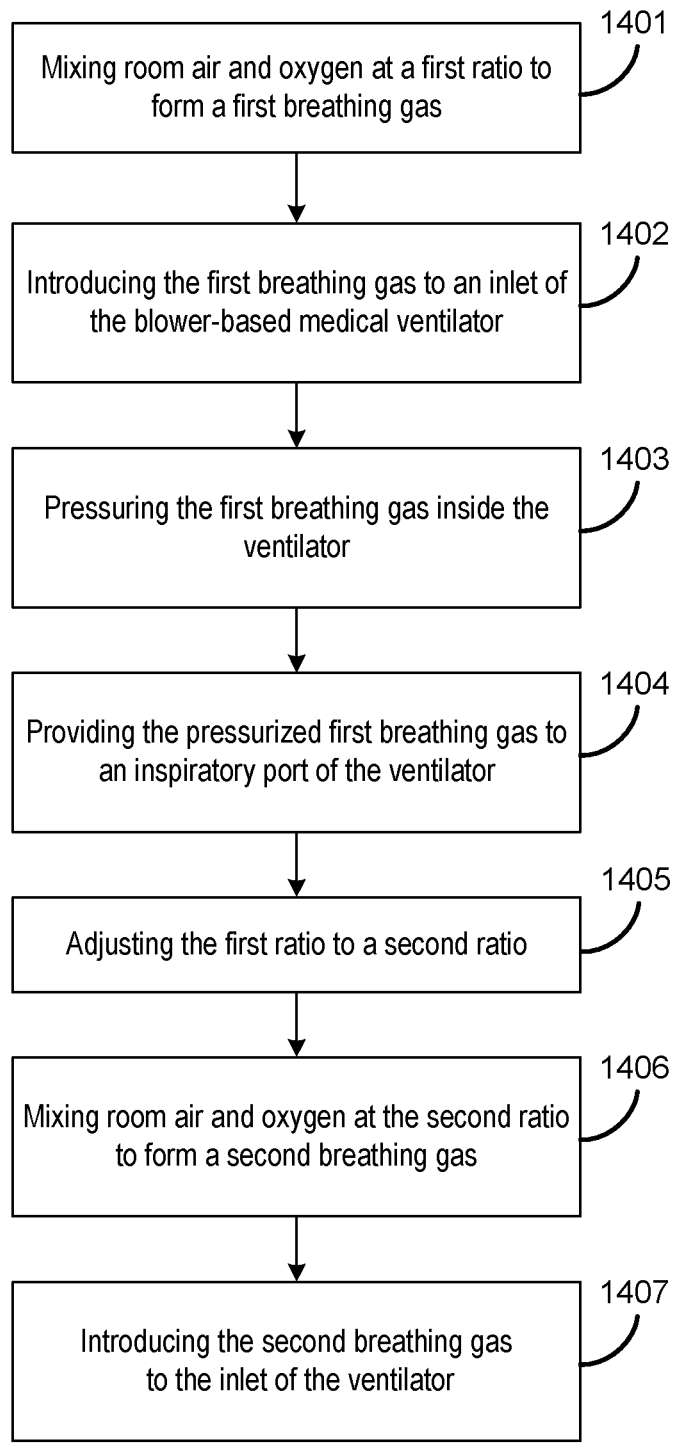
FIG. 14 is a flowchart of a method for regulating breathing gases for a blower-based medical ventilator, according to an embodiment of the present disclosure.
Figure 15:
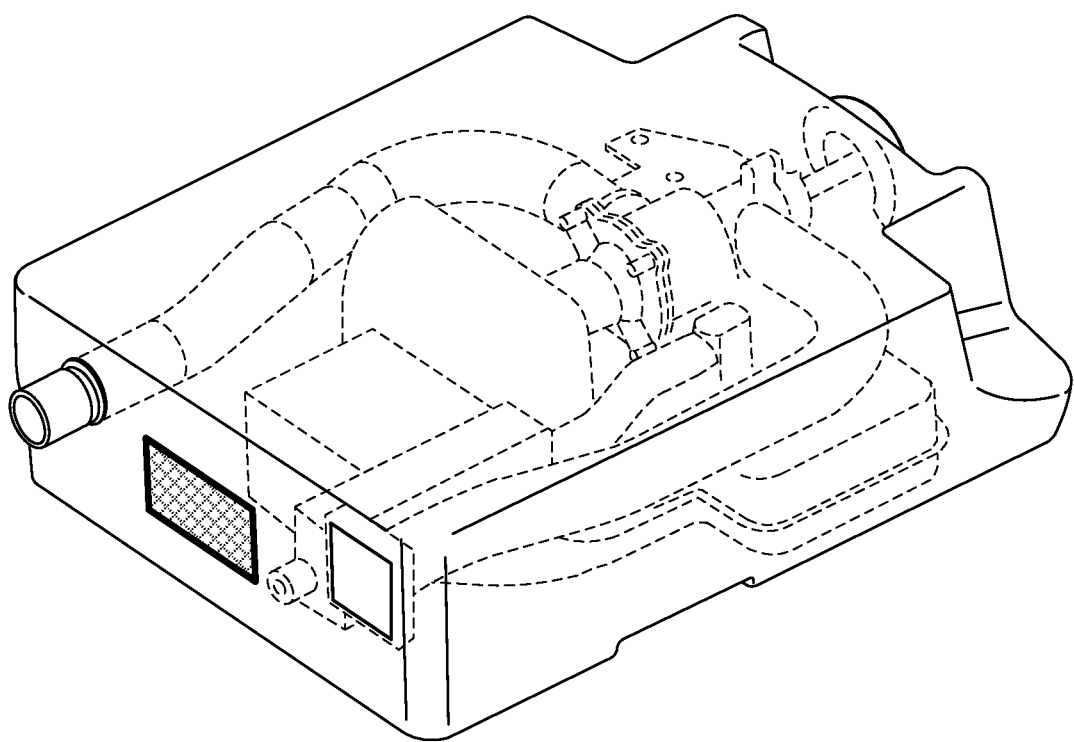
FIGS. 15, 16, and 17 are alternate embodiments of FIGS. 7, 8, and 9 with some adjustments to valve placement and other internal couplings and components.
Figure 16:
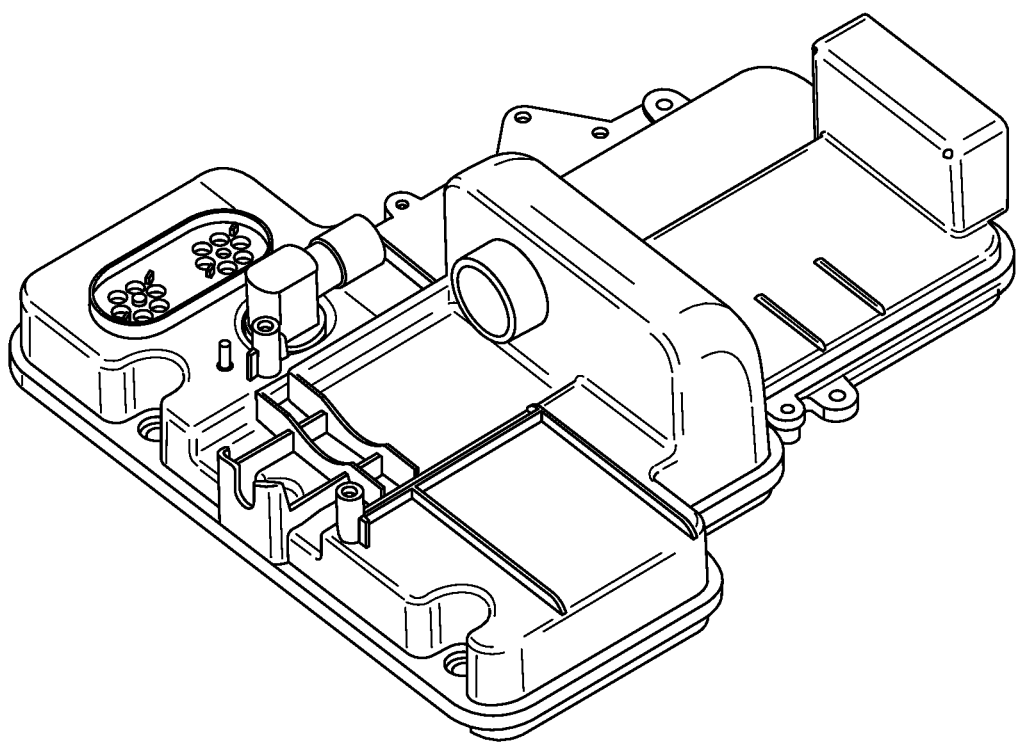
Figure 17:
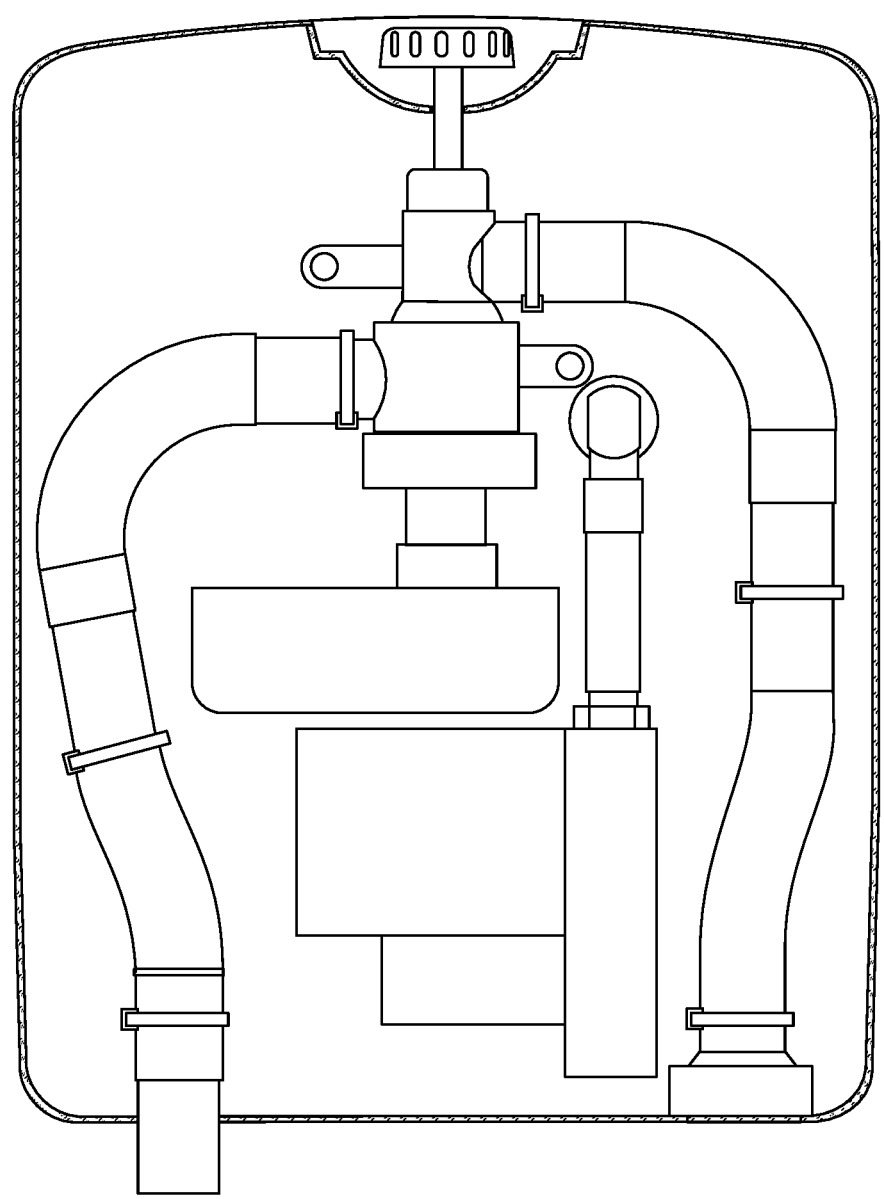

FIG. 14 shows a method 1400 for regulating breathing gases for a blower-based medical ventilator, according to an embodiment. The method 1400 includes mixing room air and oxygen at a first ratio to form a first breathing gas (1401). The first breathing gas passes through a gas flow path upstream of the blower-based ventilator. The method also includes introducing the first breathing gas to an inlet of the blower-based medical ventilator (1402), and pressurizing the first breathing gas inside the blower-based medical ventilator (1403). The method also includes providing the pressurized first breathing gas to an inspiratory port of the blower-based medical ventilator (1404). The method includes adjusting the first ratio to a second ratio (1405), which is different from the first ratio. This is done upstream and separate from the blower-based ventilator. Adjustment can be done manually by a user (such as by adjusting a control knob) or automatically by a digital controller (such as a control circuit that compares a measured FiO2 to a target FiO2 and controls an actuator such as a motor that adjusts the globe valve to achieve the target FiO2 concentration). The method also includes mixing room air and oxygen at the second ratio to form a second breathing gas (1406), and introducing the second breathing gas to the inlet of the blower-based medical ventilator (1407). Introducing breathing gas to the inlet of the ventilator is accomplished by connecting an outlet of a gas regulator to the inlet of the ventilator.

Embodiments of the ventilator system described herein enable breathing gases to be mixed upstream of and outside of a medical ventilator. The gas regulator mixes air and oxygen to a desired ratio outside of and independent from the ventilator. The gas mixing is invisible to the ventilator, which draws air through its environmental inlet just as it did without the gas regulator. The ventilator is designed to draw ambient air from the environment where the ventilator is operating, and the gas regulator changes that ambient air without moving the ventilator into a different environment. The gas mixing (provided by the gas regulator) is decoupled from the ventilation (provided by the ventilator). This design enables the two devices to operate independently. Further, the gas regulator can be attached to existing ventilators, such as ventilators already in use in clinical settings, without modification to those existing ventilators.

The gas regulator may be described as a gas mixer, mixing system, or accumulator. It provides a reservoir or buffer of mixed air upstream of the ventilator, at a desired concentration or ratio, that is available for the ventilator to use to deliver a breath to a patient. The descriptions above describe mixing oxygen and room air, but other gases can be mixed as well, such as heliox (a breathing gas composed of a mixture of helium (He) and oxygen ($O_2$)) or nitrox (a breathing gas with nitrogen, such as 68% nitrogen (N) and 32% oxygen ($O_2$)). These different gases have different densities and thus a different regulator may be provided for each; that is, one regulator devoted to air mixed with concentrated oxygen, a second separate regulator for air mixed with heliox, and so on for other gas mixtures.

In an embodiment, the gas regulator effectively changes the oxygen content in the room air that supplies the ventilator. Ambient air is typically about 21% FiO2. The gas regulator can boost this amount up to 100% FiO2 by mixing the room air with concentrated oxygen. In an embodiment, the mixing valve of the gas regulator operates in a range of 21% FiO2 up to 100% FiO2. For example, when the valve is turned in one direction (such as clockwise), it widens the opening between the valve and the oxygen inlet to allow more concentrated oxygen to flow into the valve, and when turned the other direction (such as counter-clockwise), it narrows the opening to reduce the amount of oxygen flowing into the valve. Thus, turning the valve changes the FiO2 of the mixed air coming out of the regulator.

In an embodiment, the gas regulator can be coupled to the air inlet of any ventilator that uses atmospheric air (ambient air or room air) and that is capable of delivering a mix of air with high-pressure oxygen (the ventilator is high-pressure oxygen compatible). In an embodiment, the gas regulator is used with a blower-based ventilator that is high-pressure $O_2$ compatible. In an embodiment, the ventilator is rated to provide pressurized oxygen up to 100% FiO2. The gas regulator provides a very low pressure (above local atmospheric pressure) (or zero pressure relative to local atmospheric) mix, and the ventilator draws from this mix instead of from the outside ambient air. The source of concentrated oxygen is connected to the gas regulator instead of to the ventilator, and as a result the oxygen is included in the air that flows into the inlet of the ventilator (upstream of the blower), instead of adding concentrated oxygen to the air flow inside the ventilator, downstream of the blower.

In an embodiment, the gas regulator is provided as an upgrade kit to enable a ventilator to be upgraded to a wider FiO2 range. Because the gas regulator is de-coupled from the ventilator, the regulator can be coupled to the ventilator (such as by coupling the outlet connector of the gas regulator to the room air inlet of the ventilator and, optionally, including mounting the gas regulator to the ventilator as a base) in the field.

The embodiments described herein may be employed using software, hardware, or a combination of software and hardware to implement and perform the systems and methods disclosed herein. Although specific devices have been recited throughout the disclosure as performing specific functions, one of skill in the art will appreciate that these devices are provided for illustrative purposes, and other devices may be employed to perform the functionality disclosed herein without departing from the scope of the disclosure. In addition, some aspects of the present disclosure are described above with reference to block diagrams and/or operational illustrations of systems and methods according to aspects of this disclosure. The functions, operations, and/or acts noted in the blocks may occur out of the order that is shown in any respective flowchart. For example, two blocks shown in succession may in fact be executrix or performed substantially concurrently or in reverse order, depending on the functionality and implementation involved.

This disclosure describes some embodiments of the present technology with reference to the accompanying drawings, in which only some of the possible embodiments were shown. Other aspects may, however, be embodied in many different forms and should not be construed as limited to the embodiments set forth herein. Rather, these embodiments were provided so that this disclosure was thorough and complete and fully conveyed the scope of the possible embodiments to those skilled in the art. Further, as used herein and in the claims, the phrase "at least one of element A, element B, or element C" is intended to convey any of: element A, element B, element C, elements A and B, elements A and C, elements B and C, and elements A, B, and C. Further, one having skill in the art will understand the degree to which terms such as "about" or "substantially" convey in light of the measurements techniques utilized herein. To the extent such terms may not be clearly defined or understood by one having skill in the art, the term "about" shall mean plus or minus ten percent.

Although specific embodiments are described herein, the scope of the technology is not limited to those specific embodiments. Moreover, while different examples and embodiments may be described separately, such embodiments and examples may be combined with one another in implementing the technology described herein. One skilled in the art will recognize other embodiments or improvements that are within the scope and spirit of the present technology. Therefore, the specific structure, acts, or media are disclosed only as illustrative embodiments. The scope of the technology is defined by the following claims and any equivalents therein.

What is claimed is:

1. A medical ventilator system comprising:
   a ventilator comprising a first environmental gas inlet, an inspiratory port, an expiratory port, and a blower, wherein the blower is located in a gas flow path between the first environmental gas inlet and the inspiratory port;
   an oxygen regulator comprising an oxygen inlet, a second environmental gas inlet, a mixing valve, a plenum upstream of the mixing valve, a pressure sensor for measuring a pressure inside the plenum, and a mixed gas outlet, wherein the mixing valve combines oxygen from the oxygen inlet and gas from the second environmental gas inlet into a mixed gas provided to the mixed gas outlet; and
   a fluidic coupling between the ventilator and the oxygen regulator for coupling the mixed gas outlet of the oxygen regulator to the first environmental gas inlet of the ventilator.

2. The system of claim 1, wherein the blower is operable to apply a negative pressure to the first environmental gas inlet of the ventilator, and wherein the negative pressure is applied to the mixed gas outlet of the oxygen regulator via the fluidic coupling.

3. The system of claim 2, wherein the negative pressure is further applied to the second environmental gas inlet of the oxygen regulator via the mixing valve.

4. The system of claim 1, wherein the oxygen regulator further comprises a pressure regulating valve between the plenum and the oxygen inlet.

5. The system of claim 1, wherein the oxygen regulator comprises a housing having a knob or hardware input coupled to the mixing valve to adjust the mixing valve.

6. The system of claim 1, wherein the ventilator comprises an interface that mounts to the oxygen regulator.

7. The system of claim 1, wherein the plenum of the oxygen regulator is defined by a rigid casing comprising between the oxygen inlet and the mixing valve.

8. A gas regulator for retrofitting a blower-based medical ventilator, the gas regulator comprising:
   a housing comprising a compressed gas inlet, an environmental gas inlet, and a mixed gas outlet;
   a plenum defined by the housing;
   a pressure sensor measuring a pressure of compressed gas inside the plenum;
   a mixing valve between the plenum and the mixed gas outlet;
   a pressure-regulating valve between the plenum and the compressed gas inlet; and
   a controller operatively coupled to the pressure-regulating valve.

9. The gas regulator of claim 8, wherein the controller receives the measured pressure from the pressure sensor.

10. The gas regulator of claim 9, wherein the controller is programmed to adjust the pressure-regulating valve upon determining that the measured pressure is less than a threshold.

11. The gas regulator of claim 8, further comprising a user-adjustable hardware input mechanically coupled to the mixing valve.

12. A method of configuring a medical ventilator, comprising:
- providing a gas regulator comprising an oxygen inlet, an air inlet, a mixing valve, and a mixed gas outlet;
- fluidically coupling a source of compressed oxygen gas to the oxygen inlet of the gas regulator;
- fluidically coupling the mixed gas outlet of the gas regulator to an environmental gas inlet of the medical ventilator;
- operating the mixing valve to combine the compressed oxygen gas with air from the air inlet at a first ratio, to form a mixed gas; and
- providing the mixed gas to the environmental gas inlet of the medical ventilator, wherein the medical ventilator comprises a high-pressure oxygen inlet capable of being opened or closed.

13. The method of claim 12, wherein the method further comprises closing the high-pressure oxygen inlet of the medical ventilator.

14. The method of claim 12, further comprising adjusting, inside the gas regulator, a pressure of the compressed oxygen gas from a first pressure and providing the mixed gas at a second pressure that is different from the first pressure.

15. The method of claim 14, wherein the second pressure that is lower than the first pressure.

16. The method of claim 14, further comprising adjusting a pressure of the mixed gas within the medical ventilator to a third pressure different from the second pressure, and providing the pressurized mixed gas to an inspiratory port of the medical ventilator for delivery to a patient.

17. The method of claim 16, wherein the third pressure is higher than the second pressure.

18. The method of claim 16, further comprising measuring a percent concentration of oxygen (FiO2) in the mixed gas or the pressurized mixed gas, and adjusting the mixing valve according to the measured FiO2.

19. The method of claim 12, further comprising decoupling the mixed gas outlet of the gas regulator from the environmental gas inlet of the medical ventilator, and operating the medical ventilator independently of the gas regulator.

* * * * *